US008133688B2

(12) United States Patent (10) Patent No.: US 8,133,688 B2
Hakansson et al. (45) Date of Patent: Mar. 13, 2012

(54) IMMUNOREGULATION IN CANCER, CHRONIC INFLAMMATORY AND AUTOIMMUNE DISEASES

(75) Inventors: Leif Hakansson, Höllviken (SE); Birgitta Clinchy, Ljungsbro (SE)

(73) Assignee: Canimguide Therapeutics AB, Hollviken (SE)

( * ) Notice: Subject to any disclaimer, the term of this patent is extended or adjusted under 35 U.S.C. 154(b) by 0 days.

(21) Appl. No.: 13/157,215

(22) Filed: Jun. 9, 2011

(65) Prior Publication Data
US 2011/0287969 A1 Nov. 24, 2011

Related U.S. Application Data

(63) Continuation of application No. 12/777,133, filed on May 10, 2010, now Pat. No. 7,960,126, which is a continuation of application No. 11/785,821, filed on Apr. 20, 2007, now abandoned, which is a continuation of application No. PCT/SE2005/001582, filed on Oct. 20, 2005.

(30) Foreign Application Priority Data

Oct. 20, 2004 (SE) ...................... 0402536

(51) Int. Cl.
G01N 33/53 (2006.01)
(52) U.S. Cl. ....... 435/7.1; 435/7.92; 435/7.93; 435/7.94
(58) Field of Classification Search ........................ None
See application file for complete search history.

(56) References Cited

U.S. PATENT DOCUMENTS

| | | | |
|---|---|---|---|
| 5,284,750 A | 2/1994 | Silvestrini et al. | |
| 6,737,057 B1 | 5/2004 | Zaghouani | |
| 7,960,126 B2 * | 6/2011 | Hakansson et al. | ............ 435/7.1 |
| 2003/0021792 A1 | 1/2003 | Roben et al. | |
| 2005/0153329 A1 | 7/2005 | Hakansson et al. | |

FOREIGN PATENT DOCUMENTS

| | | |
|---|---|---|
| JP | 62-016430 | 1/1987 |
| JP | 2005089325 | 4/2005 |
| WO | WO 91/09619 | 7/1991 |
| WO | WO 00/28072 | 5/2000 |
| WO | WO 02/30465 | 4/2002 |
| WO | WO 03/099312 | 12/2003 |
| WO | WO 2004/048933 | 6/2004 |
| WO | WO 2006/043891 | 4/2006 |
| WO | WO 2006/110091 | 10/2006 |
| WO | WO 2008/136736 | 11/2008 |

OTHER PUBLICATIONS

Shinoda et al. Immunopathological role of pulpal tissue components in periapical pathosis. I. Detection of "new "antigens in modified dog pulpal extracts. Journal of Endodontics, 12(11):528-533, 1986.*
Anderson, et al., "Contributions of the Mac-1 Glycoprotein Family to Adherence-Dependent Granulocyte Functions: Structure-Function Assessments Employing Subunit-Specific Monoclonal Antibodies" The Journal of Immunology, Jul. 1, 1986, pp. 15-27, vol. 137 No. 1.
Bajpai, et al., "Immunomodulating Activity of Analogs of Noninflammatory Fragment 163-171 of Human Interleukin-1 B", Immunopathology, 1998, 38:237-245.
Belluco, et al., "Interleukin-6 Blood Level Is Associate With Circulating Carcinoembryonic Antigen and Prognosis in Patients With Colorectal Cancer" Annals of Surgical Oncology, 2000, pp. 133-138, vol. 7, No. 1.
Bhol, et al., "The autoantibodies to alpha 6 beta 4 integrin of patients affected by ocular cicatricial pemphigoid recognize predominantly epitopes within the large cytoplasmic domain of human beta 4." J. Immunol. Sep. 1, 2000;165(5):2824-9.
Brevig, et al., "The recognition of adsorbed and denatured proteins of different topographies by beta2 integrins and effects on leukocyte adhesion and activation." Bismaterials. Jun. 2005;26(16):3039-53.
Brocks et al., "Radioimmunoassay of Laminin in Serum and its Application to Cancer Patients", Clinical Chemistry, 1986, 32/5: 787-791.
Chung, et al., "Serum Interleukin-6 Levels Reflect the Disease Status of Colorectal Cancer" Journal of Curgical Oncology, 2003, pp. 222-226, vol. 83.
Cioli, et al., "A New Protein Antidenaturant Agent, Bindarit, Reduces Secondary Phase of Adjuvant Arthritis in Rats", Journal of Rheumatology 1992 vol. 19, No. 11 pp. 1735-1742.
Clinchy, et al., "Preoperatvie interleukin-6 production by mononuclear blood cells predicts survival after radical surgery for colorectal carcinoma." Cancer. May 1, 2007;109(9):1742-9.
Davis, et al., "The α4β1 integrin can mediate leukocyte adhesion to casein and denatured protein substrates" Journal of Leukocyte Biology, 1997, pp. 318-328, vol. 62.
Davis, George E., "The Mac-1 and p150, 95 β2 Integrins Bind Denatured Proteins to Mediate Leukocyte Cell-Substrate Adhesion" Experimental Cell Research, 1992, pp. 242-252, vol. 200.
Drachenberg et al., "Circulating Levels of Interleukin-6 in Patients with Hormone Refractory Prostate Cancer", The Prostate, 41:127-133 (1999). (Abstract).
Galizia, et al., "Prognostic Significance of Circulating IL-10 and IL-6 Serum Levels in Colon Cancer Patients Undergoing Surgery" Clinical Immunology, Feb. 2002, pp. 169-178, vol. 102, No. 2.

(Continued)

*Primary Examiner* — Maher Haddad
(74) *Attorney, Agent, or Firm* — Knobbe, Martens, Olson & Bear, LLP

(57) ABSTRACT

The present invention primarily relates to a method for analyzing the amount of immunoregulatory integrin binding factors and/or patient endogenous antibodies which are directed against such factors, the factors having the capacity to modulate the immune functions in a subject suffering from cancer or inflammatory or autoimmune diseases, by utilizing binding reagents to determine these factors and/or the patient endogenous antibodies which are directed against such factors, whereby the prognosis and/or the therapeutic efficacy of any treatment of a subject suffering from cancer or inflammatory or autoimmune diseases can be determined and/or monitored. The invention further relates to the use of therapeutically active compounds for eliminating, inhibiting or enhancing such binding factors for the manufacture of pharmaceuticals to be used in the treatment of cancer, inflammatory conditions or autoimmune diseases.

6 Claims, 22 Drawing Sheets

OTHER PUBLICATIONS

Gruel, et al., "Bypassing tumor-specific and bispecific antiboides: triggering of antitumor immunity by expression of anti-FcγR scFv on cancer cell surface" *Gene Therapy* (2001) 8: 1721-1728.

Håkansson, A. et al., "Biochemotherapy of metastatic malignant melanoma. Predictive value of tumor-infiltrating lymphocytes" British Journal of Cancer, 2001, pp. 1871-1877, vol. 85, No. 12.

Håkansson, A. et al., "Tumor-infiltrating lymphocytes in metastatic malignant melanoma and response to interferon alpha treatment" British Journal of Cancer, 1996, pp. 670-676, vol. 74.

Hauptman, et al., "Antibodies to human albumin in cirrhotic sera." J. Clin Invest. Jul. 1974;54(1):122-7.

Kaminska, et al., "Clinical Significance of Serum Cytokine Measurements in Untreated Colorectal Cancer Patients: Soluble Tumor Necrosis Factor Receptor Type I—An Independent Prognostic Factor" Tumor Biology, 2005, pp. 186-194, vol. 26.

Kaminska, et al., "CRP, TNFα, IL-1ra, IL-6, IL-8 and IL-10 in Blood Serum of Colorectal Cancer Patients" Pathology Oncology Research, 2000, pp. 38-41, vol. 6, No. 1.

Kinoshita, et al., "Serum Interleukin-6 Level Reflects the Tumor Proliferative Activity in Patients with Colorectal Carcinoma" Cancer, Jun. 15, 2009, pp. 2526-2531, vol. 85, No. 12.

Kuntz, "Structure-based strategies for drug design and discovery." Science. 1992 257(5073):1078-1082.

Maccio et al., "High Serum Levels of Soluble IL-2 Receptor, Cytokines, and C Reactive Protein Correlate with Impairment of T Cell Response in Patients with Advanced Epithelial Ovarian Cancer", Gynecological Oncology, 1998, 69: 248-252.

Miller, et al., "Ligand binding to proteins: the binding landscape model." Protein Sci. Oct. 1997;6(10):2166-79.

Nikiteas, et al., "Serum IL-6, TNFα and CRP levels in Greek colorectal cancer patients: Prognostic implications" World Journal of Gastroenterology, 2005, pp. 1639-1643, vol. 11.

Oyama, et al., "Autoantibodies to extracellular matrix protein 1 in lichen sclerosus." Lancet. Jul. 12, 2003;362(9378):118-23.

Piancatelli, et al., "Local Expression of Cytokines in Human Colorectal Carcinoma: Evidence of Specific Interleukin-6 Gene Expression", Journal of Immunotherapy, 1999, vol. 22, p. 25-32.

Rich, et al., "Elevated Serum Cytokines Correlated with Altered Behavior, Serum Cortisol Rhythm, and Dampened 24-Hour Rest-Activity Patterns in Patients with Metastatic Colorectal Cancer" Clinical Cancer Research, Mar. 1, 2005, pp. 1757-1764, vol. 11.

Rouard, et al, "Fc Receptors as Targets for Immunotherapy" *Intern. Rev. Immunol.* (1997) 16: 147-185.

Ruka, et al., "Alterations of routine blood tests in adult patients with soft tissue sarcomas: Relationships to cytokine serum levels and prognostic significance" *Annals of Oncology* (2001) 12: 1423-1432.

Saso, et al., "Inhibition of Protein Denaturation by Fatty Acits, Bile Salts and Other Natural Substances: A New Hypothesis for the Mechanism of Action of Fish Oil in Rheumatic Diseases" Japan Journal of Pharmacology, 1999, vol. 79 pp. 89-99.

Siedlar, et al., "Depressed Tumor Necrosis Factor Alpha and Interleukin-12p40 Production by Peripheral Blood Mononuclear Cells of Gastric Cancer Patients: Associate with IL-IR-Associated Kinase-1 Protein Expression and Disease State", Internation Journal Cancer, 2005, vol. 114, p. 144-152.

Tamura, et al., "Anti-albumin antibodies in sera of patients with liver disease." Gastroenterol Jpn. Oct. 1982;17(5):469-75.

Ueda, et al., "Serum levels of cytokines in patients with colorectal cancer: Possible involvement of interleukin-6 and interleukin-8 in hematogenous metastasis" *J. Gastroenterol.* (1994) 29: 423-429.

Wood et al., "The Clinical Significance of the Pattern of Elevated Serum Carcinoembryonic Antigen (CEA) Levels in Recurrent Colorectal Cancer", BR. J. Surg., 1980, 67(1): 46-48 (Abstract).

Wu et al., "Serum Interleukin-6 Levels Reflect Disease Status of Gastric Cancer", American Journal of Gastroenterology, 1996, 91(7): 1417-1422 (Abstract).

International Search Report, dated Nov. 4, 2003, issued in PCT/SE03/00869.

International Search Report, dated Feb. 6, 2006, issued in PCT/SE05/001582.

International Search Report, dated Jul. 13, 2006, issued in PCT/SE06/000440.

International Preliminary Report on Patentability, date Dec. 4, 2006, issued in PCT/SE06/000440.

International Search Report, dated Jan. 5, 2009, issued in PCT/SE08/000314.

* cited by examiner

IMMUNOREGULATION IN CANCER, CHRONIC INFLAMMATORY AND AUTOIMMUNE DISEASES

RELATED APPLICATIONS

This application is continuation of and claims the benefit of priority to U.S. patent application Ser. No. 12/777,133, filed May 10, 2010 now U.S. Pat. No. 7,960,126, which is a continuation of and claims the benefit of priority to U.S. patent application Ser. No. 11/785,821, filed Apr. 20, 2007 now abandoned, which is a continuation of and claims the benefit of priority to International Patent Application No. PCT/SE2005/001582, filed Oct. 20, 2005, which designated the United States and was published in English and, which claims the benefit of priority to Swedish Patent Application No. 0402536-7, filed Oct. 20, 2004. All of the aforementioned applications are hereby expressly incorporated by reference in their entireties.

FIELD OF THE INVENTION

The present invention relates to a method for determining the presence of integrin binding factors, the preparation of a pharmaceutical composition controlling said factors, and the use of said pharmaceutical composition in therapeutic treatment of diseases characterized by a deregulation of immune reactivity such as immunosuppression in cancer patients and/or an over-reactive immune reactivity as in patients with inflammatory or autoimmune diseases.

BACKGROUND OF THE INVENTION

Initiation of an Immune Response

The reactivity of the immune system is finely tuned in order to control an over-reactivity to normal tissues (self) resulting in autoimmune or chronic inflammatory diseases. At the same time new structures, e.g. infectious agents, virus infected cells, cancer cells (non-self) have to be recognised in order that an immune response is mounted. The initiation of a specific immune response is a well-orchestrated chain of events where multiple cell types interact. Antigen presenting cells take up, process and present peptides of a foreign antigen, in the context of the major histocompatibility complex (MHC), to lymphoid cells with unique receptors (T-cell receptor, TCR). These events culminate in the activation of effector functions such as the release of cytokines, production of specific antibodies and/or cellular cytotoxic activity.

The circulation of immune cells via the blood stream and lymphatics, from one peripheral (secondary) lymphoid tissue to another, and then to peripheral inflammatory sites, is a prerequisite, both for the initiation of the immune response and for efficient effector functions. Recirculation of immune cells and their recruitment to tissues are dependent on and regulated by adhesive interactions between these cells and vascular endothelial cells and extravascular connective tissue. These adhesive interactions are governed by the expression and activation of various adhesion molecules expressed on the cell membranes.

Integrins

Integrins are a superfamily of transmembrane glycoproteins found predominantly on leukocytes that mediate cell-cell and cell substratum interactions. They play an important role in the initiation and regulation of an immune response, tissue recruitment and migration of inflammatory cells and cytotoxic activity of lymphocytes. Integrins are heterodimers consisting of noncovalently associated $\alpha$ and $\beta$ subunits. They are organized in subfamilies based on their $\beta$ chain. The members of the $\beta2$ subfamily (LFA-1, Mac-1, p150,95 and $\alpha d\beta 2$) have the same $\beta$ subunit (CD18) but separate $\alpha$ subunits. All four molecules play a role in the inflammatory process. In addition, LFA-1 (Leukocyte Function Associated molecule-1, CD11a/CD18) is involved in adhesion of cytotoxic T cells to their target cells. Mac-1 (CR3, CD11b/CD18) is involved in phagocytosis and p150,95 (CD11c/CD18) is important for B cell activation. Their ligands consist of the cellular counter-receptors ICAM-1, ICAM-2 and ICAM-3 as well as fibrinogens, endotoxins, Factor X and the complement protein C3bi. Additional molecules with binding capacity to some of the $\beta 2$ integrins are the soluble form of CD23 (low affinity receptor for IgE) and soluble CD16 (Fc $\gamma$ receptor III). Although the integrins are constitutively expressed, they exist in a low-affinity state. A high-affinity state can be induced by clustering of the receptors or by a change in receptor conformation. Blockade of integrins will seriously influence initiation of an immune response, recruitment of inflammatory cell to tissues, migration of these cells within tissues and the cytotoxic activity of cells of the immune system.

Immunosuppression in Cancer

Malignant tumours manage to suppress immune mediated anti-tumour reactivity. The function of immune cells in cancer patients is thereby impaired. Generally this is more pronounced in tumour infiltrating mononuclear cells, TIMC, than in cells obtained from peripheral blood. It has for example repeatedly been demonstrated that the proliferative response to mitogens, such as phytohemagglutinin (PHA) or concanavalin A (ConA), is inhibited, natural killer cell (NK-cell) activity and cytotoxic activity of CTLs are reduced as is the maturation and function of dendritic cells and the immune balance seems to be directed to a T-helper 2 situation. Immunosuppression of TIMC can, however, at least to some extent be overcome in vitro, either by washing, preincubation before stimulation, or culturing in interleukin-2. Amazingly, the down regulation of the immune system, which relates to cancer, does not result in a seriously increased incidence of infectious diseases in these patients. Reasonably due to a regional systemic gradient of immunosuppressive agents.

Extracts or supernatants from tumours are often immunosuppressive. Several factors have been suggested to mediate this suppression, e.g., TGF-$\beta$, PGE$_2$, IL-10, IL-4 and others, either being produced by the tumour cells as such or by tumour-infiltrating lymphocytes (TIL) or tumour associated macrophages (TAM). However, no fundamental mechanism has been identified so far.

During early stages, primary malignant tumours (or inoculates) can progress locally without giving rise to metastatic disease. This is compatible with the occurrence of regional immunosuppression with sustained systemic immune reactivity (so called concomitant immunity), indicating a regional—systemic gradient of immunosuppression. Systemic immunosuppression can thus be regarded as a systemic dissemination, or "spillover" of intra—tumoural suppression.

Immunosuppression in cancer patients appears already at an early stage: Immune parameters predicting the recurrence of radically operated renal cell carcinoma patients can be demonstrated already one week after primary radical surgery. Analysis of the sentinel node of breast cancer patients at primary surgery shows low numbers of dendritic cells (DC) and down-regulation of the zeta-chain of TCR. In addition, function parameters of circulating monocytes are down-regulated in stage II primary breast cancer patients.

The immunosuppression of cancer patients described above often involves an ongoing systemic, chronic inflammation with a pathological production of several cytokines, in particular IL-6 and TNF-α seems to be important mediators in this process. This results in a paraneoplastic syndrome with a poor performance status—impaired general condition, which is characterized by anorexia, fatigue, subfebrility and distortion of various biochemical laboratory parameters, e.g., low haemoglobin concentration, high numbers of platelets, increased numbers of blood monocytes, increased concentration of acute phase reactants, increased c-reactive protein (CRP) and erythrocyte sedimentation rate (ESR) and other factors. For cancer patients this condition is correlated to the tumour burden of the patient, being worse in more advanced disease. In the clinical situation, attempts are often made to ameliorate the poor general condition of these patients by corticosteroid treatment.

Immune reactivity is normally down-regulated when the eliciting antigenic structures are eliminated. In progressive cancer, however, the opposite situation prevails as the antigenic structures of the tumour cells are not eliminated. The mechanisms for "cancer related" immunosuppression are still largely unknown.

Autoimmunity and Chronic Inflammation

From basic immunology it is known that the reactivity of the immune system is finely tuned (self-tolerance) in order to control an over reactivity to normal tissues otherwise resulting in autoimmune diseases. Tolerance to normal tissues is maintained by central eradication of "forbidden clones" and various mechanisms are active in maintaining peripheral tolerance.

Abnormalities in the induction or maintenance of self-tolerance thus lead to immune responses to self antigens and autoimmune diseases. These diseases, such as rheumatoid arthritis, multiple sclerosis and type I diabetes, count among the major medical problems of industrialized societies. Antibodies reactive with self-antigens, like DNA and immunoglobulin, as wells as T cells with reactivity towards self antigens, for example myelin basic protein, are found. Similar to the situation with progressive cancer, in autoimmune disease the antigenic structures (the self antigens) do not disappear. However, instead of a down regulation of the immune response in these diseases, the reactivity continues resulting in destruction of normal tissues. The etiology and immunoregulatory mechanisms of most autoimmune diseases remain unknown.

Therapeutic Possibilities in Cancer

Some malignant tumours, immunogenic tumours, can be recognised by the immune system as non-self and an immune response to these tumours is mounted. When such tumours start to grow progressively the immune control has been lost, but can in about 20 percent of these patients be reactivated by immunostimulatory treatment, e.g. interferon-alpha or interleukin-2.

As mentioned above, tolerance to normal structures is maintained by central eradication of "forbidden clones" and various mechanisms are active in maintaining peripheral tolerance, for example signalling via CTLA4 and regulatory CD4+CD25+ lymphocytes. Therapeutic strategies interfering with these mechanisms might result in some enhancement of anti-tumour reactivity but at the cost of an increased autoimmune reactivity.

Chronic inflammatory reactions in cancer patients often result in a poor response to the immunotherapy. There are some animal and human reports on the importance of the immune status of tumour bearers for response also to chemotherapy or radiotherapy. Immunostimulatory treatment of the dysregulated immune system of cancer patients might be counter-productive. If the immune system in cancer is directed to downregulation of the chronic inflammatory reaction there is a risk that further therapeutic immunostimulation will enhance the immunosuppression and thereby further downregulate the immune reactivity against the tumour cells. The strategy should therefore be to eliminate mediators of immunosuppression before the immune system is stimulated. In the present invention, such immunoregulatory factors are described. Strategies to minimise the pathological production or biological activity of such immunoregulatory factors being immunosuppressive in cancer patients include treatment with enzyme inhibitors, monoclonal antibodies or fragments thereof, synthetic constructs or signal transduction inhibitors.

Therapeutic Possibilities in Chronic Inflammatory or Autoimmune Disease

Therapy for autoimmune diseases consists mainly of anti-inflammatory drugs, particular corticosteroids and antibodies directed against inflammatory cytokines. In severe cases, immunosuppressive drugs, such as cyclosporin are used to block T cell activation. Plasmapheresis has also been used to reduce the levels of circulating antibodies or immune complexes. Thus, no therapy directed to the fundamental dysregulatory mechanism is available. The present invention describes factors, the lack of which will result in an uncontrolled activity of an inflammatory process. Administration of these factors to patients with chronic inflammatory or autoimmune disease will be of value to control the over-reactivity in these diseases.

SUMMARY OF THE PRESENT INVENTION

The present invention discloses in one aspect thereof a method for analyzing the amount of integrin binding factors and/or patient endogenous antibodies directed against such factors, present and produced in tissues of cancer patients or tissues of patients with chronic inflammatory or autoimmune diseases, said factors having the capacity to modulate the immune functions in a subject suffering from cancer or inflammatory or autoimmune diseases, whereby the prognosis and/or the therapeutic efficacy of any treatment of a subject suffering from cancer or inflammatory or autoimmune diseases can be determined and/or monitored, said factors and/or the patient endogenous antibodies directed against such factors being determined by utilizing any analysis method commonly known per se to determine these factors and/or the patient endogenous antibodies directed against such factors.

The term "integrin binding factors" used herein means "integrin binding or blocking factors" or "integrin binding factors" or "integrin blocking factors", which are a type of cell surface receptor binding or blocking factors.

The term "immune functions" used in this context preferably include immune initiation, antibody production, modulation of the production of cytokines. binding of inflammatory cells to endothelial cells, migration of inflammatory cells in tissues, cytotoxic activity of immune cells.

The term "tissue" used herein means any tissue including blood, serum, body liquors, soft and hard tissue present in a patient.

In another preferred embodiment the integrin binding factors are β2-integrin or α4β1 integrin binding or blocking factors.

In another preferred embodiment the integrin binding factor is an integrin binding factor alone or in complex with Fc-receptor binding or blocking factors of immunoglobulins.

In another preferred embodiment binding reagents used for the determination of the integrin binding factors are externally produced antibodies, monoclonal antibodies and/or fragments thereof, or any synthetic constructs or reagents directed to these said factors, which reagents are present in liquid or solid phase.

In another preferred embodiment masspectrometry analysis includes SELDI-TOF or MALDI-TOF analysis.

In another preferred embodiment binding reagents used for the determination of patient endogenous antibodies directed against integrin binding factors, are selected from the group of binding reagents; binding to the epitope and/or antigenic site of integrin factors, externally produced antibodies, monoclonal antibodies and/or fragments thereof, and any synthetic constructs or reagents directed to these tissue related antibodies.

In another preferred embodiment cell surface substances, including integrins, are biotinylated, dissolved in the presence of a protease inhibitor and placed on a streptavidin coated surface, whereupon a determination of the binding of an antibody directed against a specific cell surface substance in the presence of a binding or blocking factor is made, whereby the amount of antibodies bound is an inverse measure of the amount blocking and/or binding factors present.

In another preferred embodiment cell surface binding factors present in a tissue sample of a patient after adsorption to said coated surface are determined.

In another preferred embodiment the amount of such integrin binding factors and/or patient endogenous antibodies directed against such factors, is used to determine the prognosis of a subject suffering from cancer.

In another preferred embodiment the amount of such integrin binding factors and/or patient endogenous antibodies directed against such factors, is used to determine the therapeutic efficacy of any cancer treatment.

In another preferred embodiment the amount of such integrin binding factors and/or patient endogenous antibodies directed against such factors, is used to determine the prognosis of a subject suffering from chronic inflammatory or autoimmune diseases.

In another preferred embodiment the amount of such integrin binding factors and/or patient endogenous antibodies directed against such factors, is used to determine the therapeutic efficacy of any treatment of chronic inflammatory or autoimmune diseases.

A further aspect of the invention relates to a use of therapeutically active substances of the group of compounds consisting of externally produced monoclonal antibodies and/or fragments thereof, synthetic constructs, protease inhibitors and signal transduction inhibitors preventing, inhibiting and/or enhancing the activity of integrin binding factors or group of compounds producing such activity in situ, and/or patient endogenous antibodies directed against such factors, which are involved in the dysregulation of immune functions, in the manufacture of a pharmaceutical composition for the therapeutic control of such integrin binding factors and/or patient endogenous antibodies directed against such factors.

In another preferred embodiment to minimise the pathological production or biological activity of such integrin binding factors being immunosuppressive in cancer patients to enhance the therapeutic control of a malignant tumour in a subject suffering from a cancer.

In another preferred embodiment the therapeutically active substances comprise compounds directed against β2-integrin or α4β1 integrin binding or blocking factors.

In another preferred embodiment the therapeutically active substances comprise compounds directed against integrin binding factor alone or in complex with Fc-receptor binding or blocking factors.

In another preferred embodiment the therapeutically active substances comprise integrin binding factors or fragments thereof.

In another preferred embodiment to achieve therapeutic control in a subject suffering from chronic inflammatory or autoimmune disease to enhance the performance status of the patient.

In another preferred embodiment the therapeutically active substance is a compound enhancing the activity of integrin binding factors which are involved in the dysregulation of immune functions.

In another preferred embodiment the therapeutically active substances comprise integrin binding factors or fragments thereof.

In another preferred embodiment the therapeutically active substances comprise β2-integrin binding or blocking factors, including fragments thereof.

In another preferred embodiment the therapeutically active substances comprise integrin binding factor alone or in complex with Fc-receptor binding or blocking factors.

In another preferred embodiment the therapeutically active substances comprise binding compounds directed against patient endogenous antibodies directed against such factors.

In another preferred embodiment such a therapeutically active substance is selected from the group of compounds; binding to the epitope and/or antigenic site of integrin factors, externally produced monoclonal antibodies and/or fragments thereof, synthetic constructs, and signal transduction inhibitors.

A still further aspect of the invention relates to a method of therapeutic treatment by administering therapeutically active substances preventing, inhibiting and/or enhancing the activity of integrin binding factors and/or patient endogenous antibodies directed against such factors, involved in the dysregulation of immune functions, to a subject suffering from a cancer where said immune functions are suppressed, whereby the amount of such integrin binding factors are therapeutically controlled to minimise pathological production or biological activity of such integrin binding factors being immunosuppressive, to enhance the therapeutic control of a malignant tumour in a subject suffering from a cancer, or to a subject suffering from chronic inflammatory or autoimmune diseases where said immune function is over-reactive/enhanced, whereby such therapeutically active substances preventing, inhibiting and/or enhancing the activity of integrin binding factors and/or patient endogenous antibodies are therapeutically administered to enhance the performance status of the patient and/or or to achieve therapeutic control in a subject suffering from inflammatory or autoimmune diseases.

DETAILED DESCRIPTION OF THE INVENTION

Figure 1:
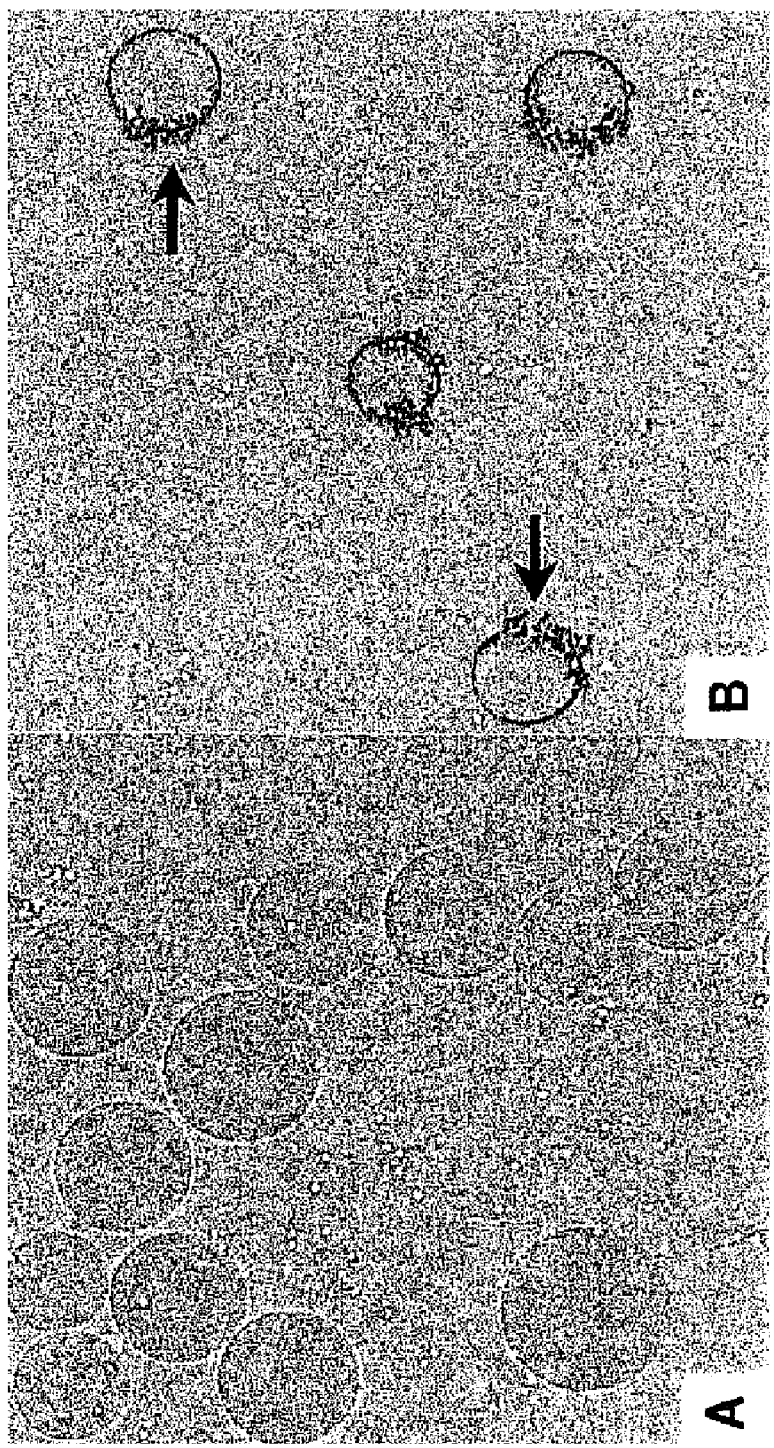
FIG. 1. PMA stimulated PBMCs from healthy persons bind to sepharose spheres coated with denatured (B) but not native human serum albumin (A).

Denatured normal proteins such as human serum albumin, ovalbumin, transferrin, fibronectin etc have been demonstrated to expose structures which bind to receptors on a monocyte cell line (Davis 1992, Davis 1997). It was furthermore demonstrated in these papers that binding of the denatured proteins could be efficiently inhibited by monoclonal antibodies directed to β2-integrins or to α4β1 integrin. A similar effect of such antibodies on the binding of granulocytes to albumin coated latex beads has been reported (Anderson 1986). We have previously shown (PCT/SE2003/00869) that immune system dysregulatory factors are generated by proteolytic fragmentation of various normally occurring substances such as albumins, immunoglobulins and hemoglobulins. It can thus be assumed that proteolytic fragmentation of these proteins results in the appearance of neo-structures, which are identical to those which appear when proteins, for example albumins are denatured. The occurrence of integrin binding factors, as a result of an increased proteolytic activity, 'was thus postulated to be generated in cancer patients.

Integrin binding factors will play an important role in the regulation of inflammation and immune reactivity as these factors will inhibit the initiation of an immune response, tissue recruitment and migration of inflammatory cells and cytotoxic activity of immune cells. Most likely, these factors will also be of importance in modulating the activation of vascular endothelial cell and thereby. have further influence on recruitment of inflammatory cells to tissues. As the proteolytic activity is increased in inflammation as well as in malignant tumours these factors will be generated under such conditions. In benign inflammatory reactions the generation of such factors will play an important role in downregulating the activity. As immune mediated anti-tumour reactivity is crucial for tumour control in cancer patients, down-regulation of this reactivity by integrin binding factors will result in tumour escape. This is thus a mechanism, which can explain most of the phenomena of immunosuppression in cancer. It is in very good agreement with our previous results showing that the occurrence of CD4+ lymphocytes in tumours correlates with response to immunotherapy, prolonged time to progression and prolonged overall survival (Hakansson 1996, Hakansson 2001) (European patent no: EP 0824 69681, U.S. Pat. No. 6,114,128).

In the present invention it is shown that tumour extracts and cancer patient sera contain integrin binding factors related to structures appearing by denaturation or proteolytic fragmentation of normally occurring proteins. Diagnostic determination of these factors will have profound prognostic value. The inhibition of their production or biological activity will significantly improve spontaneous or therapeutically induced immune mediated tumour control. In addition, the structures appearing when these-factors are generated will efficiently control the immune reactivity in chronic inflammatory and autoimmune diseases.

In the following the term tissue means whole blood, serum, plasma, lymphatic fluid, saliva, urine, faeces, ascites, pleural effusion, pus, as well as any tissue, including inflammatory cells.

Further the term artificial cell surface means biotinylated cell surface substances having been added and bound to a streptavidin coated surface, such as a mikrotiter plate, or a chromatography gel matrix, said bound cell surface substances forming an artificial surface being reactive to certain substances.

The invention is further illustrated by the following examples, which are not intended to be limiting.

EXAMPLE 1

Binding of Peripheral Blood Mononuclear Cells (PBMC) to Denatured Human Serum Albumin Davis demonstrated that a monocyte cell line bound to various denatured proteins in a β2-integrin dependent manner (Davis 1992). Similar results regarding the appearance of neo-epitopes of denatured Human Serum Albumin (dHSA), which bind to α4β1-integrins on leukocytes have been reported (Davis 1997). It can thus be concluded that conformational changes of normally occurring proteins result in structures binding to different types of cell receptors/integrins. These results are in good agreement with the well documented data on the wide capacity of these so called promiscuous receptors to bind different ligands. In order to be of any value in diagnostic tests and treatment of human patients, this observation has to be validated for normal human inflammatory cells. We have thus repeatedly demonstrated, using three different lots of dHSA that human PBMCs efficiently bind to dHSA coated sepharose spheres, but not to spheres coated with native human serum albumin (FIG. 1).

EXAMPLE 2

Figure 2A:
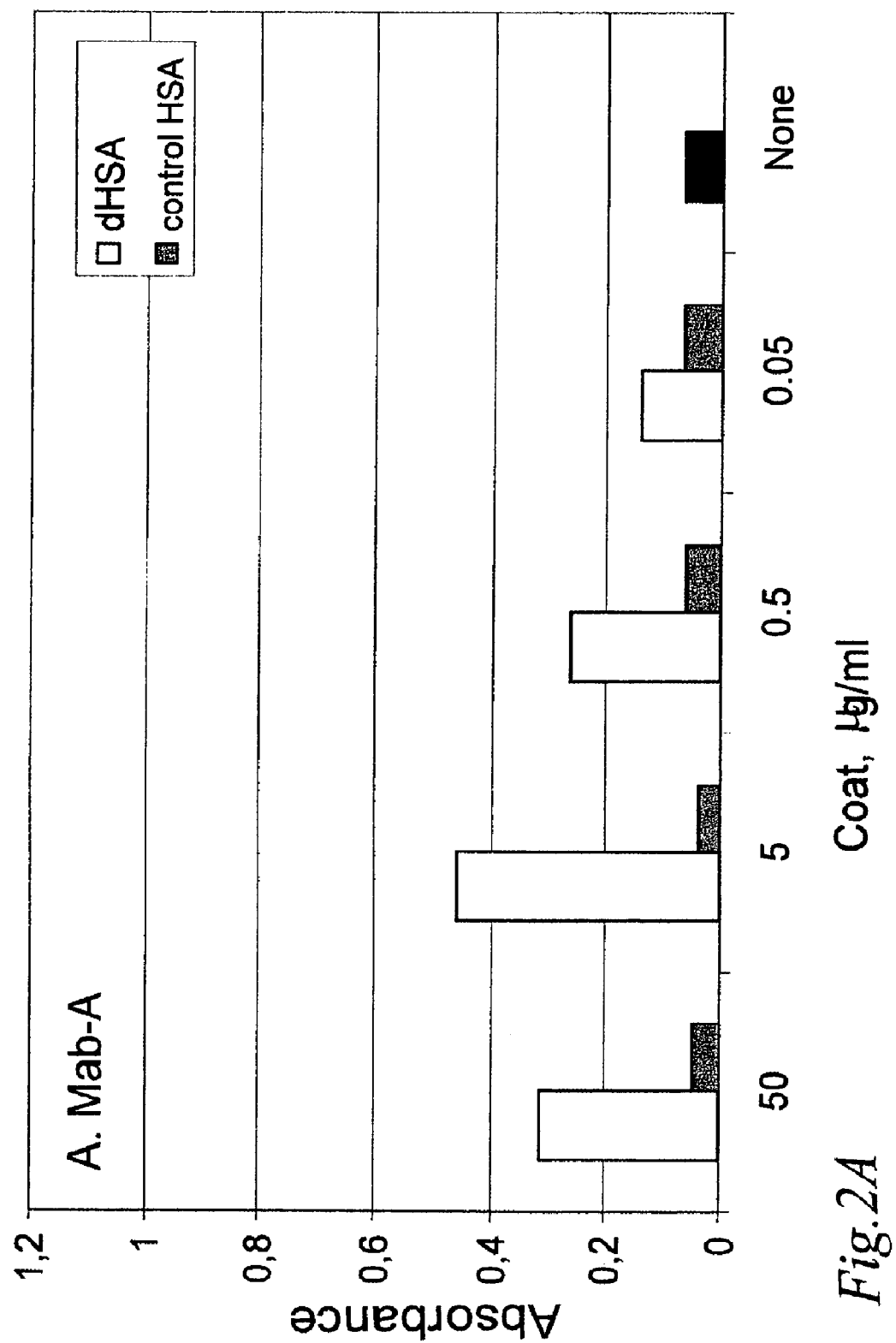
FIG. 2. ELISA for the detection of murine antibodies, mAb-A (A) and mAb-B (B) binding to human albumin. ELISA polystyrene plates were coated with denatured human serum albumin (dHSA) or native human serum albumin (controlHSA) at different concentrations.
Figure 2B:
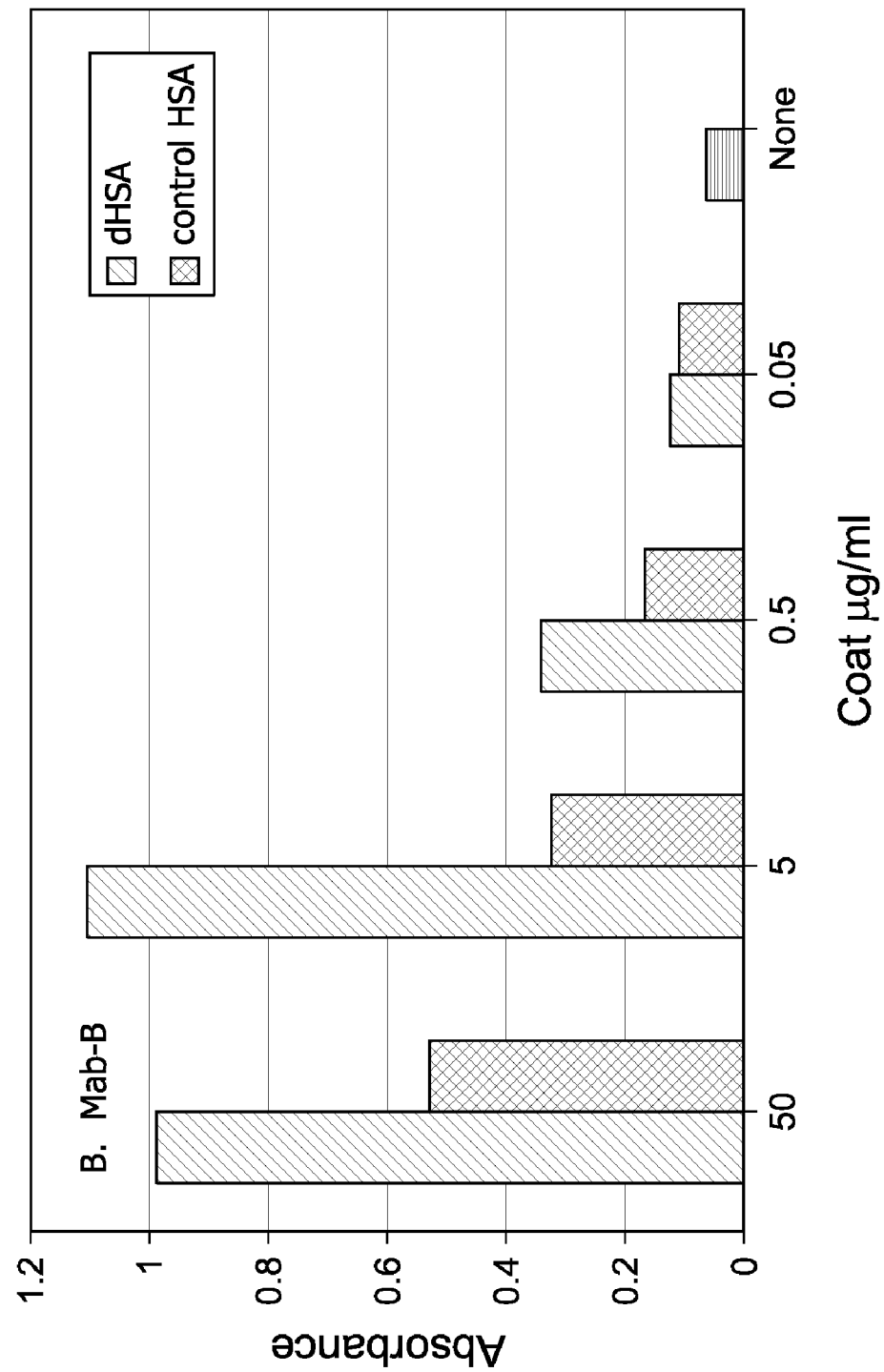

Monoclonal Antibodies Directed Against dHSA—Reactivity with Solid Chase and Cell Bound dHSA Based on the observation that dHSA binds to β2-integrins, the reactivity of two murine monoclonal antibodies of IgG1 subclass, anti-dAbclh040801 and anti-dAbclh040809 (hereinafter called mAb-A and mAb-B, respectively) specifically directed against such albumin was further characterised. Both antibodies bind to dHSA coated on polystyrene microtitre plates (FIG. 2). However, one of them (mAb-B) seems to be more efficient in binding to dHSA covalently linked to sepharose beads than the other one (mAb-A). It was demonstrated that these monoclonal antibodies actually bind to the albumin and not to impurities in the preparation of albumin from human serum as both monoclonal antibodies also bound to denatured recombinant human albumin coated on poystyrene microtitre plates.

Interestingly, when dHSA was first bound to normal PBMCs and the binding of the antibodies mAb-A and mAb-B were tested using immunocytochemistry, only one of them, mAb-A, the one with the weakest binding activity to solid phase dHSA as described in this example, was found to bind to the dHSA whereas the reactivity of mAb-B was inhibited. In addition, in the same experiment the stainability of CD18 was completely blocked by the binding of dHSA to the PBMCs.

Two conclusions can be drawn from these results: Firstly, the results of Davis are confirmed, dHSAs bind to and block the β2-integrins so that they can no longer be found by the monoclonal anti-CD18 antibody. Secondly, the two antibodies directed against dHSA bind to different epitopes as mAb-A, but not mAb-B, was found to bind. Obviously, the binding of dHSA to the cells blocks the mAb-B epitope but not the mAb-A epitope. Alternatively, all mAb-B epitopes are blocked but at least some of the mAb-A epitopes are still free to bind this antibody. Thus, it cannot be concluded from these results that the mAb-A epitope is not involved in the binding of dHSA to cells.

EXAMPLE 3

Figure 3A:
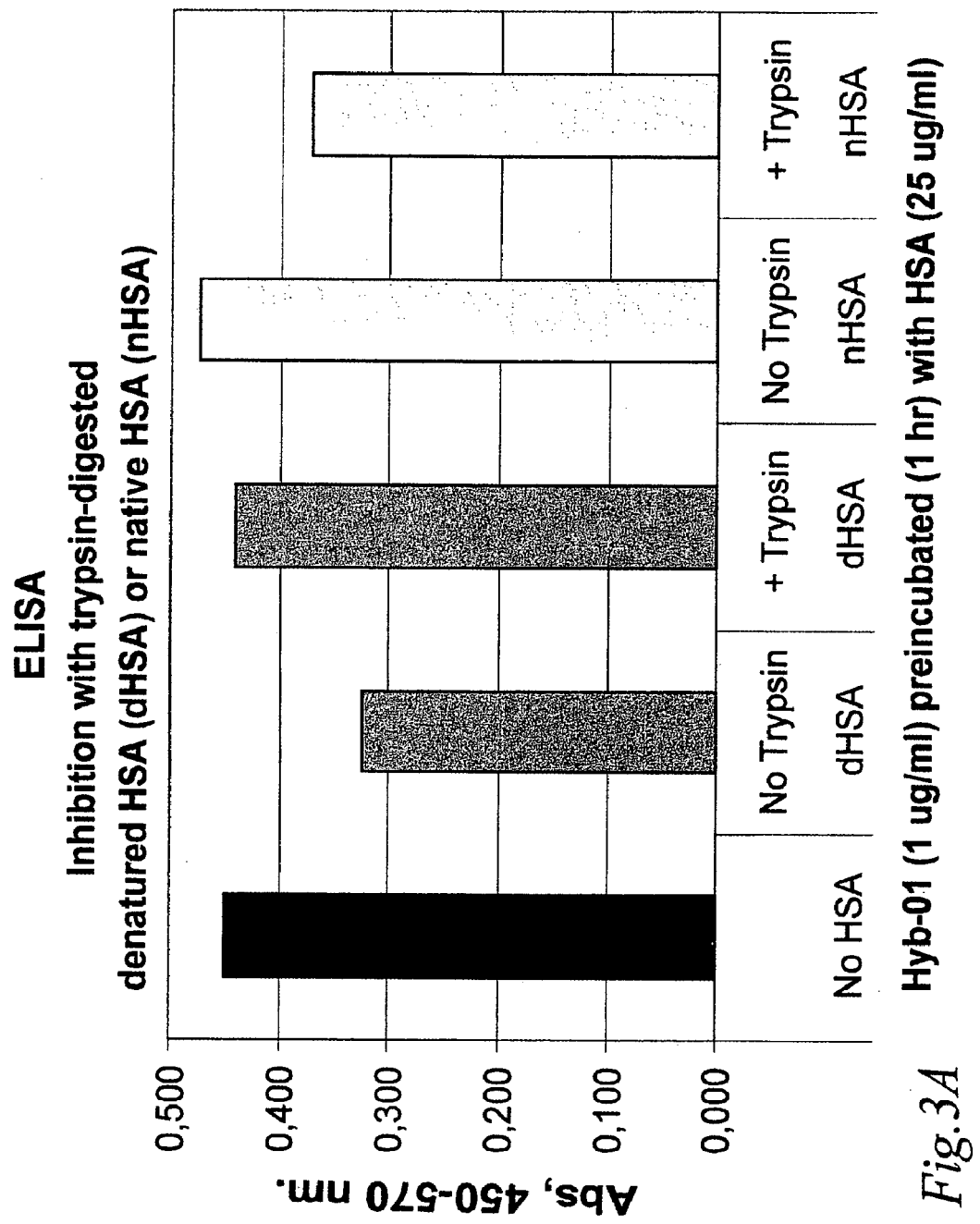
FIG. 3. A) Effect of proteolytic fragmentation of dHSA or native HSA (nHSA) on the ability of HSA to inhibit the binding of mAb-A to dHSA in an ELISA. B) Gel electrophoresis of trypsin treated HSA.
Figure 3B:
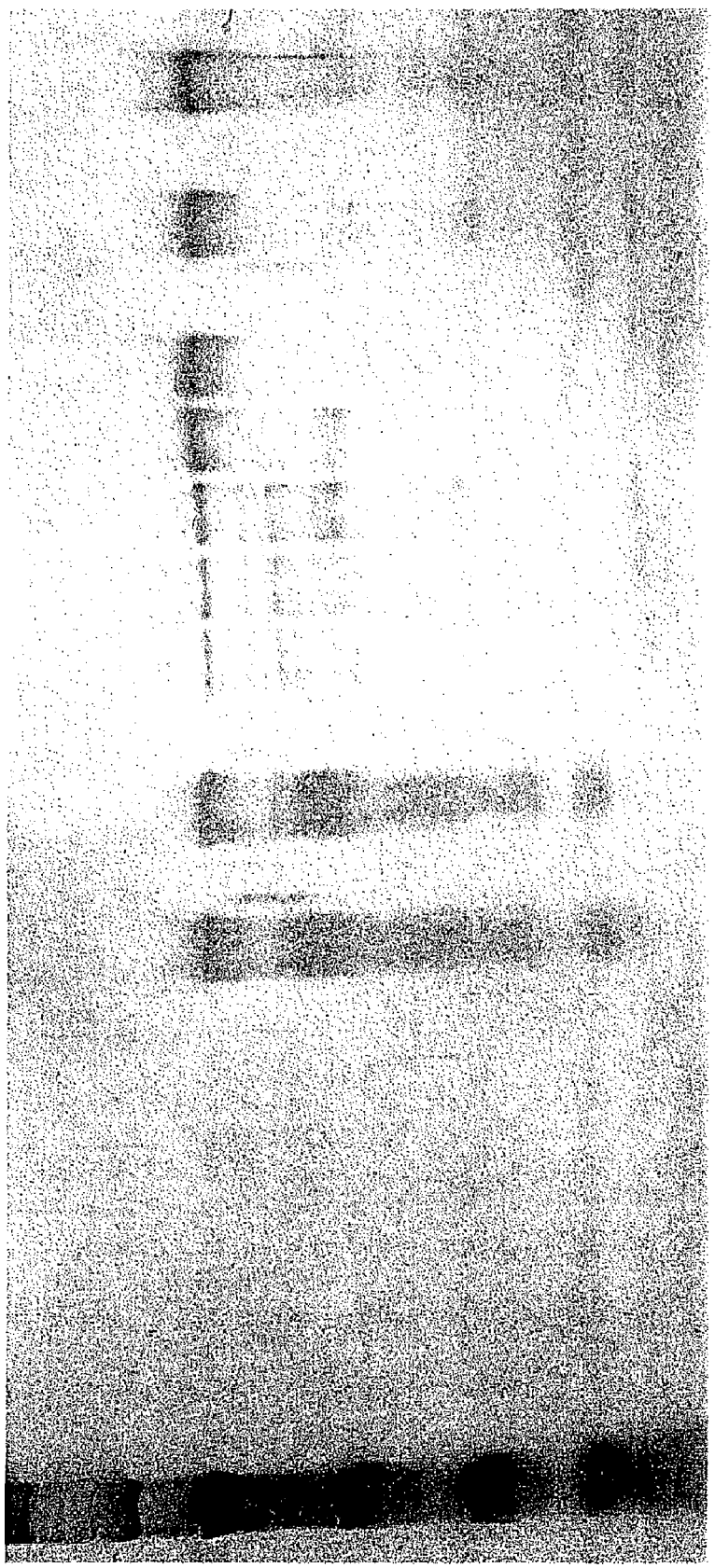

Proteolytic Fragmentation of Albumin Generates Neo-Structures to which mAbA Binds The effect of proteolytic fragmentation by trypsin on the expression of neo-structures to which mAb-A bind was analysed in an ELISA where trypsin treated albumin was pre-incubated with the antibody. Undegraded dHSA was repeatedly found to inhibit the binding of the antibody to dHSA coated plates whereas native HSA had no inhibitory effect. Trypsination reduced the inhibitory effect of dHSA but generated inhibitory structures in native HSA (FIG. 3A). This difference in the effect of trypsin is explained by the difference in sensitivity of dHSA and native HSA to proteolytic fragmentation, as shown in an electrophoretic analysis of these proteins (FIG. 3B). The dHSA is far more sensitive and is almost completely degraded in contrast to native HSA where the presence of undegraded albumin and fragments still can be demonstrated (FIG. 3B).

EXAMPLE 4

Monoclonal Antibodies Directed Against dHSA-Like Epitopes in Human Cancers

Figure 4:
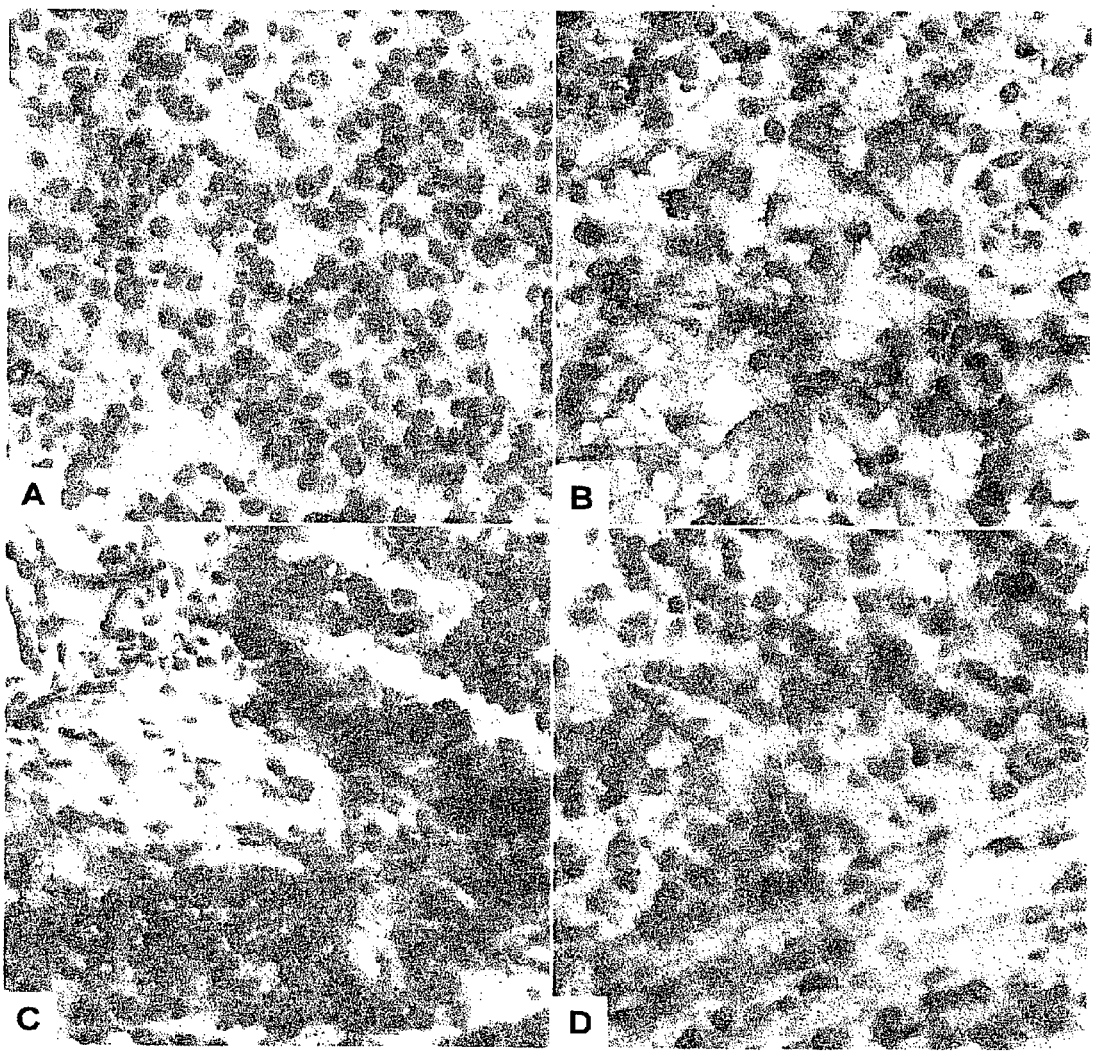
FIG. 4. Expression of the epitope detected by a monoclonal antibody directed against denatured albumin, mAb-A, in different types of human cancers: Malignant melanoma (A), renal cell carcinoma (B), colorectal cancer (C) and squamous cell carcinoma of the oral cavity (D).

Next, the occurrence of epitopes similar to those expressed on dHSA, were analysed by immunohistochemistry in malignant tumours using the monoclonal antibodies mAb-A and mAb-B. Interestingly, again one of the monoclonal antibodies, mAb-A, but not mAb-B, showed a wide reactivity in human cancers such as malignant melanoma, renal cell carcinoma, squamous cell carcinoma of the oral cavity and colorectal cancer (FIG. 4). The staining of these tumours was highly specific, but with a considerable variation between tumours of the same type and within the same tumour with some tumour cells being completely negative. In some tumours or in certain areas of the tumours the vast majority of the malignant cells were found to express the epitope. Cell nuclei were often found to be positive with a negative cytoplasm. Some vascular endothelial cells were also positive.

Figure 5:
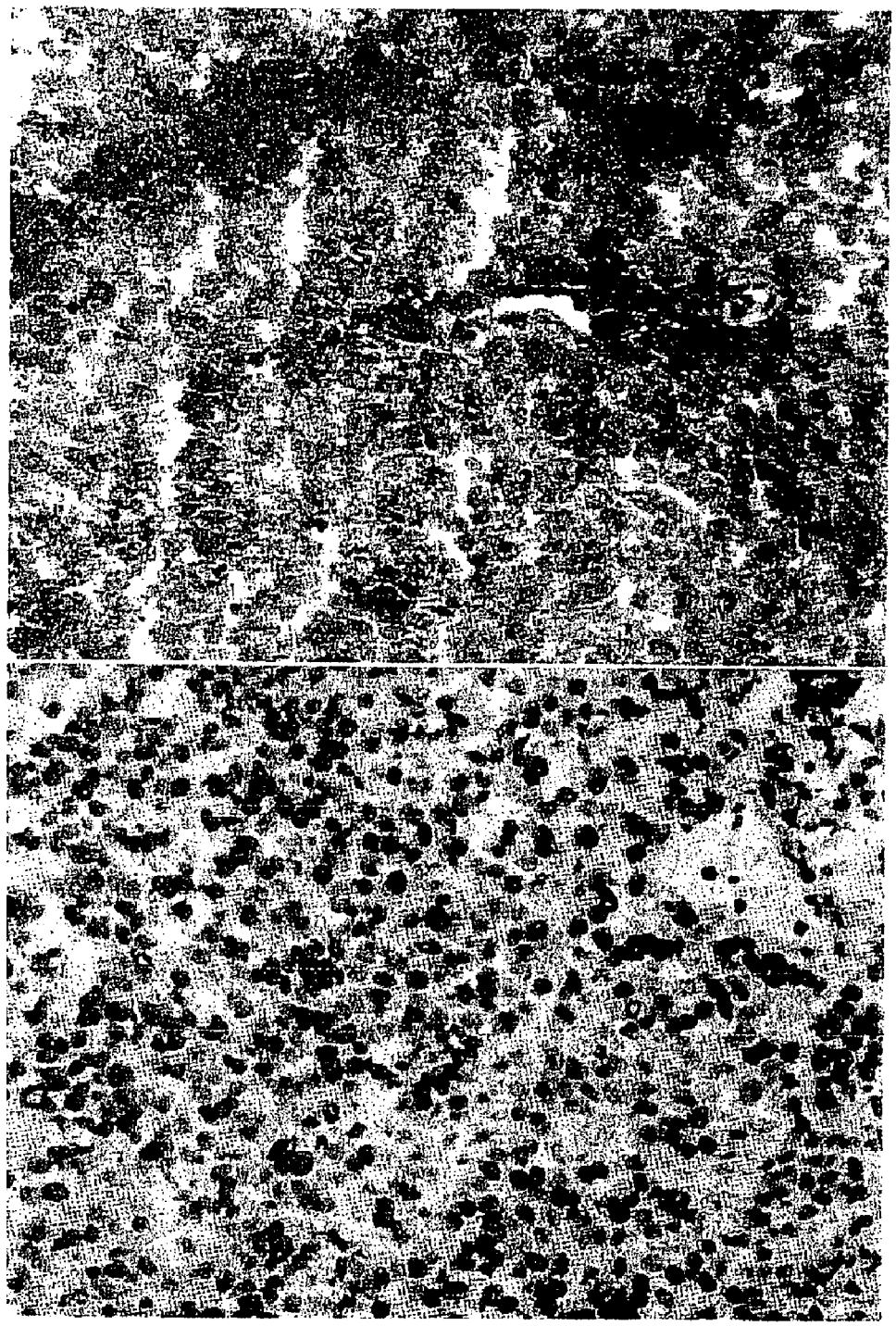
FIG. 5. Staining of the same biopsy from malignant melanoma metastases for the expression of ICAM-1 (top) and the epitope of a monoclonal antibody mAb-A directed against dHSA (bottom). Quite different staining patterns were obtained for these two antibodies, which show that the mAb-A antibody does not react with ICAM-1.

Theoretically, it could be assumed that these antibodies have a cross-reactivity with ICAM-1. However, the staining patterns of mAb-A and anti-ICAM-antibodies on tumour biopsies are quite different (FIG. 5). Thus, mAb-A does not bind to ICAM-1.

Figure 6:
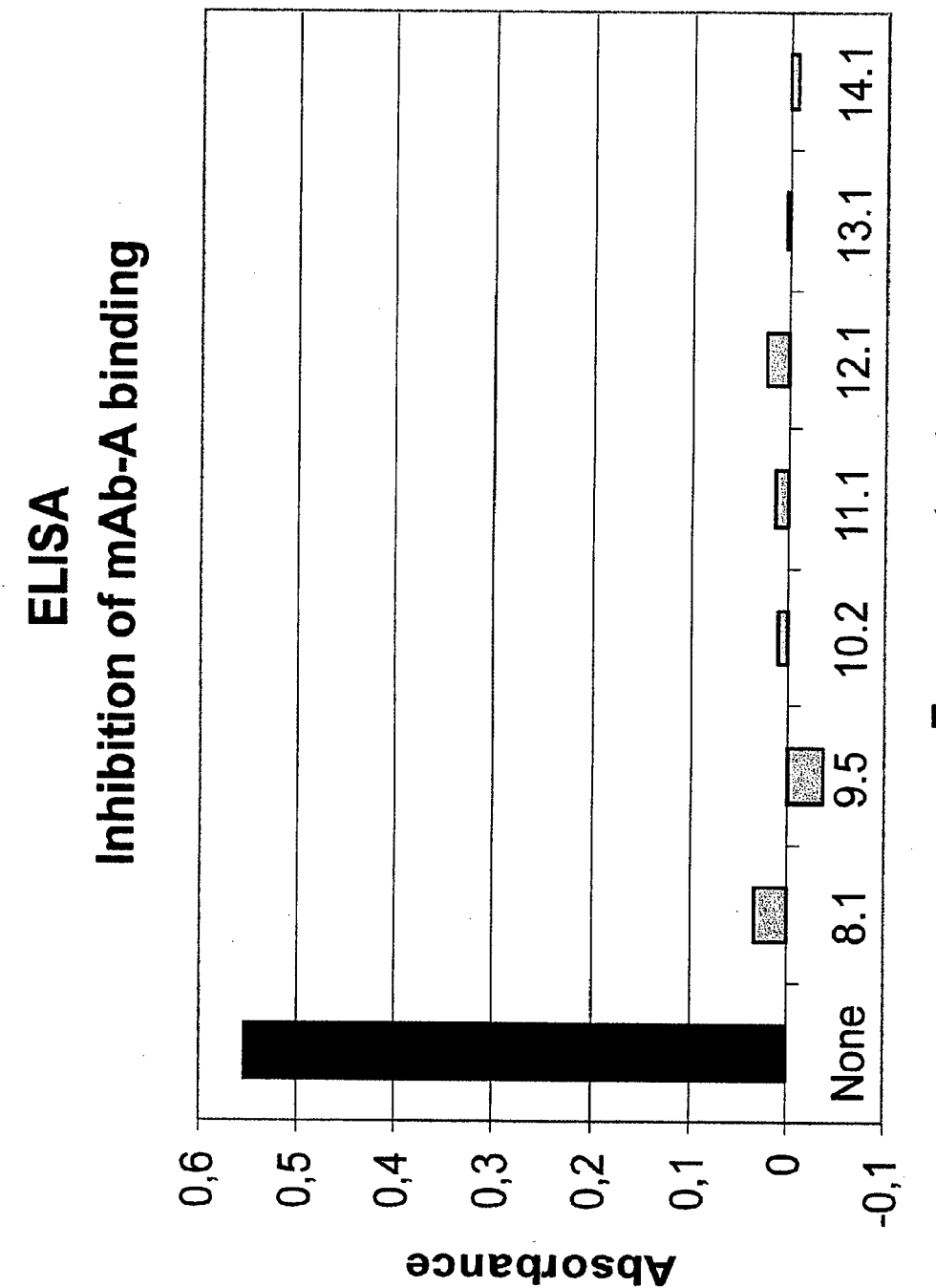
FIG. 6. Inhibition of the binding of a monoclonal antibody (directed against dHSA), mAb-A, to dHSA in an ELISA test. The binding of mAb-A is completely inhibited after pre-incubation with tumour extracts.
Figure 7:
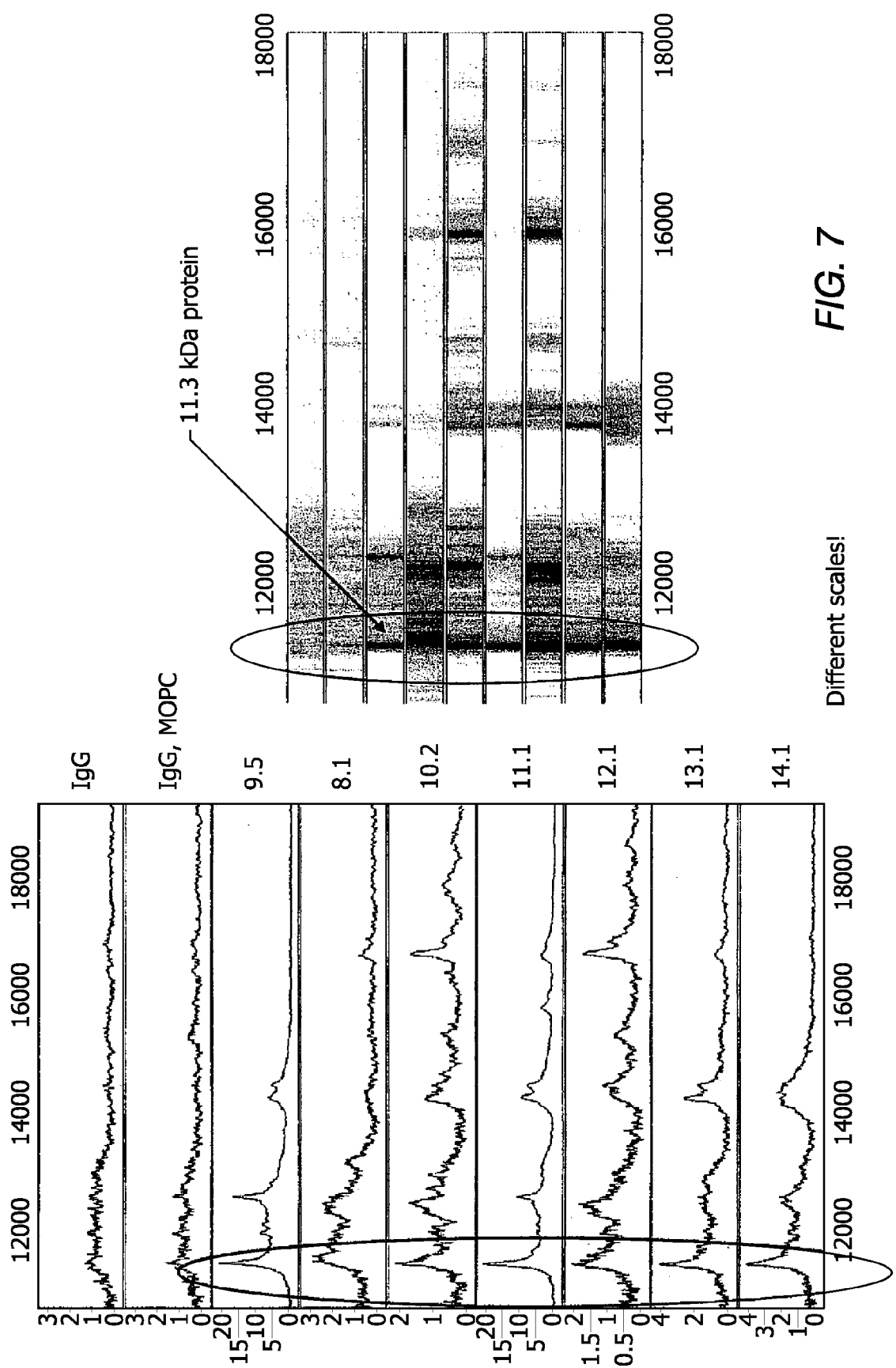
FIG. 7. Proteins captured from tumour extracts by the mAb-A using SELDI-TOF.

The occurrence of the structure/structures binding mAb-A in soluble form in tumour extracts was repeatedly demonstrated using an ELISA technique where the binding of mAb-A to dHSA coated ELISA plates was inhibited by pre-incubation with tumour extracts (FIG. 6). This epitope was further characterized using surface enhanced laser desorption/ionisation time-of-flight mass spectrometry (SELDI-TOF) where mAb-A was immobilized on a PS20 chip array and used for capture. Several substances of various sizes, which bind to the mAb-A antibody, were identified in tumour extracts obtained from six renal cell carcinomas and one malignant melanoma. An example is shown in FIG. 7. These results are highly compatible with the view that these substances are fragments produced by for example proteolytic degradation.

It can thus be concluded that the epitope detected by mAb-A is widely expressed in human cancers and can be assumed to be of importance for the biology of the malignant tumours.

EXAMPLE 5

Monoclonal Antibodies Directed a Against dHSA-Like Epitopes on Human Leukocytes

Figure 8:
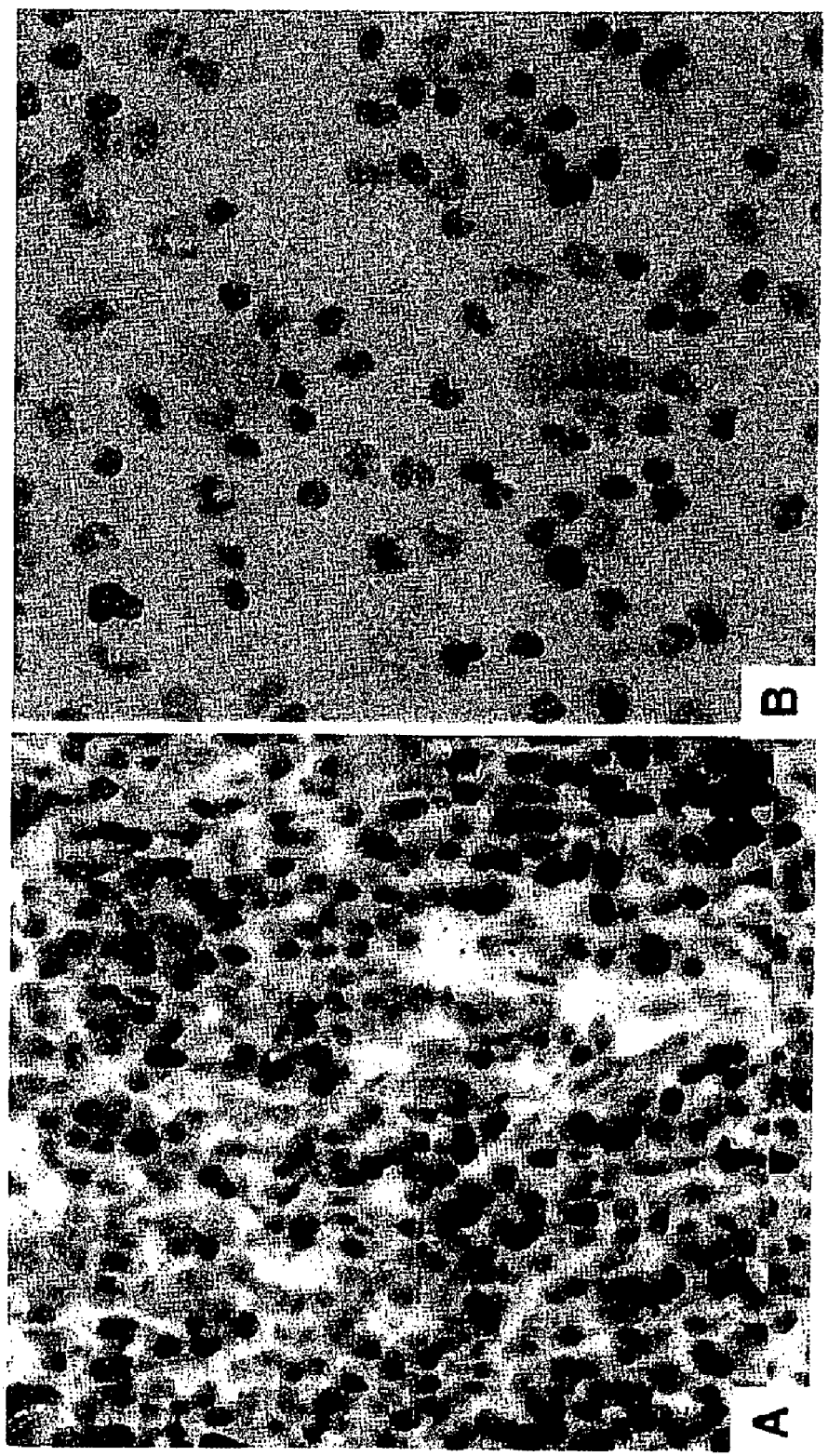
FIG. 8. Expression of the epitope detected by a monoclonal antibody directed against dHSA, mAb-A, on tumour associated lymphocytes (A) but not on blood lymphocytes from healthy controls or from cancer patients. Some monocytes express the epitope (B).

As can be seen in Example 4 above, various types of tumour cells expressed the epitope to which directed to mAb-A bind. Therefore, its expression in inflammatory cells was also analysed by immunohistochemistry. As can be seen in FIG. 8A lymphocytes and macrophages infiltrating and surrounding the tumours frequently expressed this epitope, but some of the cells in the otherwise positively stained areas were completely negative. The inflammatory cells, in contrast to some of the tumour cells, expressed this epitope mainly in the cytoplasm (FIG. 8A).

These findings were then compared with the expression of the epitope of mAb-A in purified PBMCs from healthy controls and cancer patients. The PBMCs were prepared by dextran separation and density gradient centrifugation. Cytospins preparations were then made and the PBMC were stained using mAb-A. Amazingly, the only cells, from controls as well as cancer patients, which expressed the epitope of mAb-A, were some monocytes. Lymphocytes were completely negative (FIG. 8B).

It can thus be concluded that tumour associated inflammatory cells express this epitope, which can not be found in peripheral blood lymphocytes. The reasons for this discrepancy can either be that the expression is due to a tumour related modulation of the tumour infiltrating cells or that substances expressing this epitope are present in the tumour milieu and taken up by or bound to the inflammatory cells. This of course also raises the possibility that these substances are washed away during preparation of PBMCs.

EXAMPLE 6

Determination of the mAb-A and mAb-B Specificity

Figure 9:
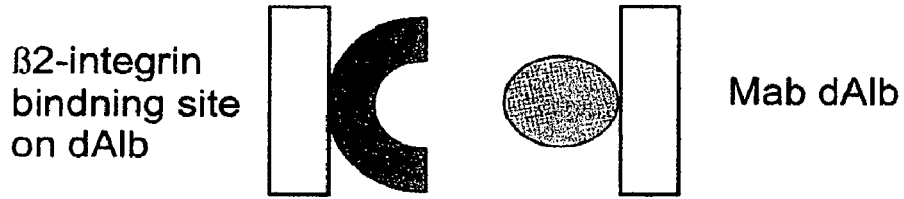
FIG. 9. Schematic drawing showing the interacting structures of the β2-integrin binding site on dHSA, the antigen binding site (idiotype) of antibodies directed against the β2-integrin binding site on dHSA, the β2-integrin and the antigen binding site (idiotype) of antibodies directed against the β2-integrin. It is thus obvious that the antibodies directed against the β2-integrin binding site on dHSA and antibodies directed against the β2-integrin have complementary structure and can thus bind to each other.
Figure 9:
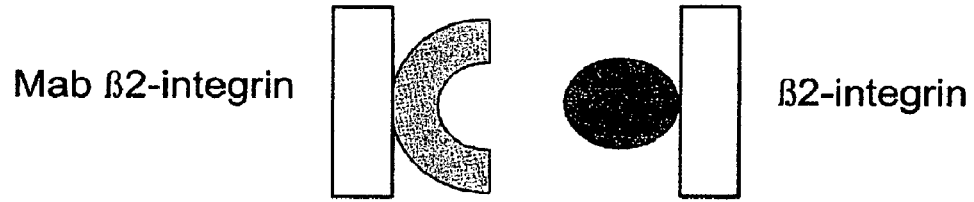

Antibodies directed against dHSA binding to the β2-integrin binding site of albumin will have a structure identical to or at least very similar to that of the β2-integrin. Thus, in analogy with idiotype anti-idiotype interaction in the idiotype network (see FIG. 9), anti-β2-integrin antibodies will recognize this structure on antibodies directed against dHSA.

Figure 10:
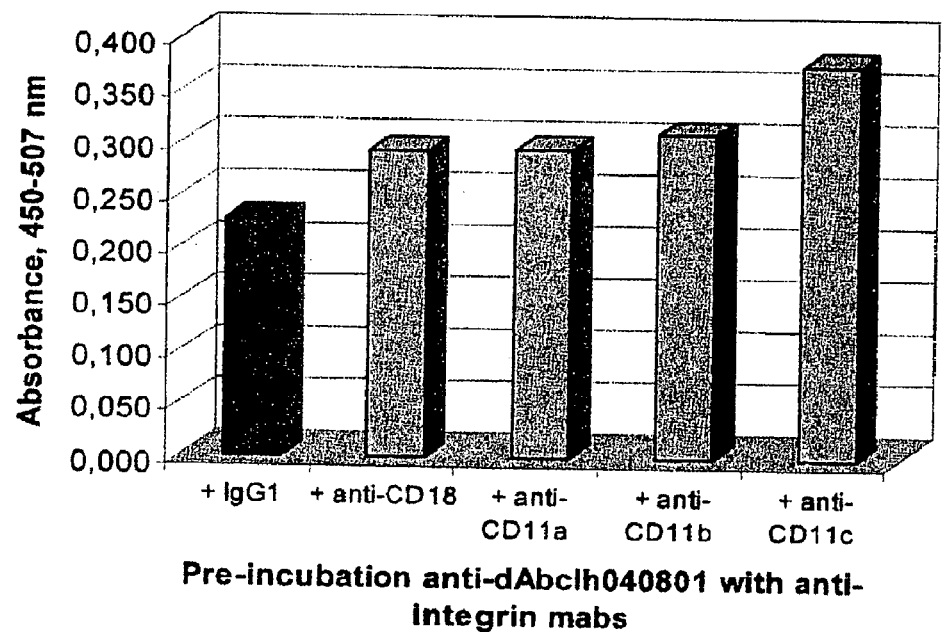
FIG. 10. Interaction of monoclonal anti-integrin antibodies with monoclonal antibodies directed against dHSA, mAb-A and MAb-B An increased amount of mouse IgG binding to dHSA was detected by ELISA when mAb-A and mAb-B were pre-incubated with antibodies directed against integrins as compared to an irrelevant control antibody (IgG1).
Figure 10:
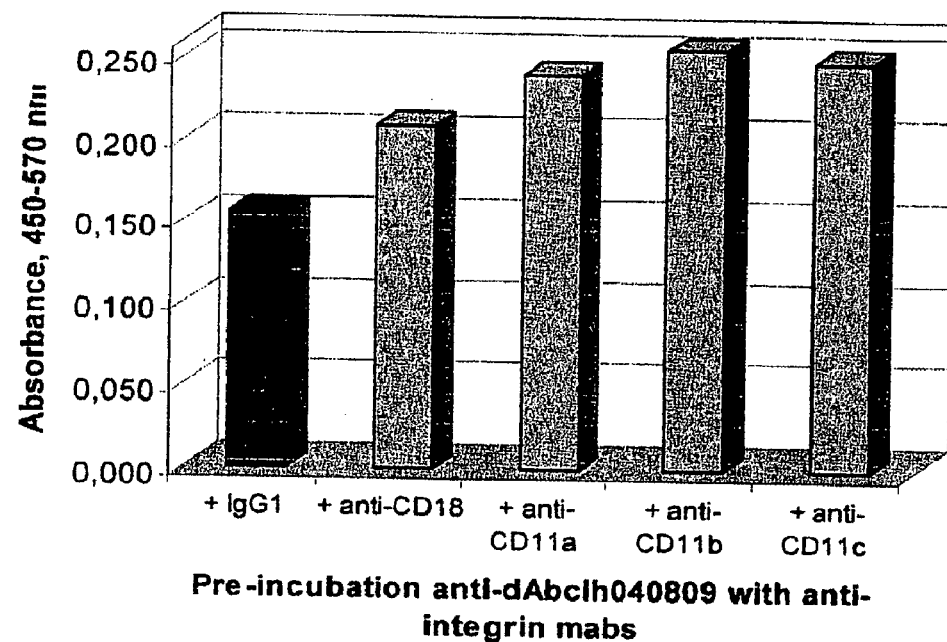

Based on these considerations, anti-β2-integrin antibodies directed against CD18, CD11a, CD11b and CD11c were mixed with mAb-A or mAb-B at equimolar concentration (1 μg/ml). After incubation for 1 h, the mixtures were then added to ELISA plates coated with dHSA. If the anti-β2-integrin antibodies recognise the idiotype of mAb-A and mAb-B, then antibody-antibody complexes will form resulting in binding of more IgG to solid phase dHSA. Compared to the control experiment where the anti-β2-integrin antibody was substituted for by a monoclonal IgG antibody of the same subclass but with irrelevant specificity, antibody-antibody complexes were demonstrated for all anti-β2-integrin antibodies with the two monoclonal antibodies mAb-A and mAb-B directed to dHSA. In particular, the anti-CD11c-antibody seems to be somewhat more efficiently binding than the others (FIG. 10).

It can thus be concluded that the specificity of the mAb-A and mAb-B antibodies are directed to or close to the β2-integrin binding site on dHSA.

EXAMPLE 7

Figure 11:
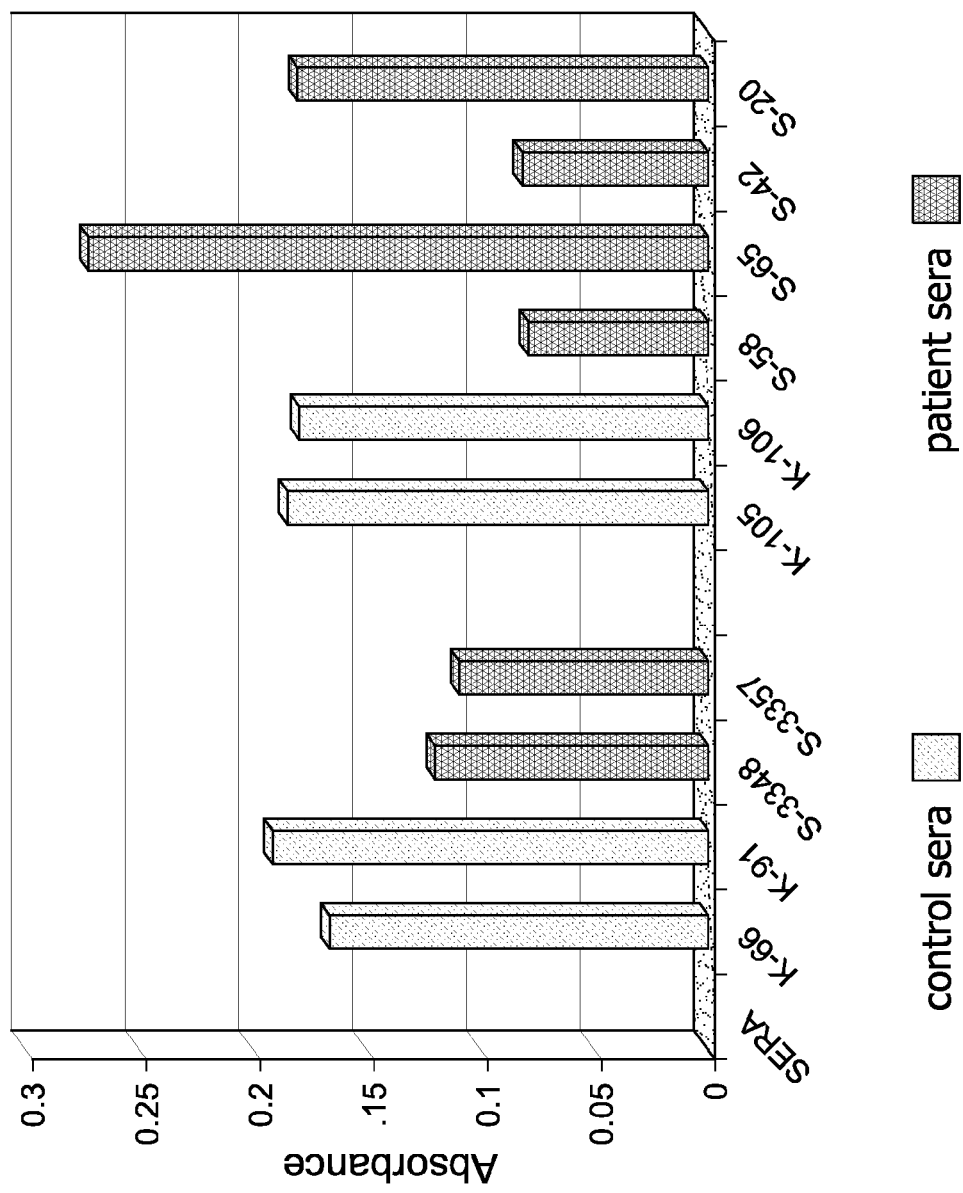
FIG. 11. Inhibition of the binding of a murine monoclonal antibody (directed against dHSA), mAb-A, to dHSA in an ELISA test. As shown, the binding is markedly inhibited by four patients' sera and stimulated by one in these experiments.

Serum Factors Interfering with the Binding of the Monoclonal Antibodies mAb-A and mAb-B to dHSA The presence of serum factors interfering with the binding of the monoclonal antibodies mAb-A and mAb-B to dHSA was analysed by incubating cancer patient and control sera with these antibodies. The incubated antibody-sera mixtures were then added to ELISA plates coated with dHSA. Two experiments including 6 cancer patient sera and 4 control sera, 2 in each experiment, were performed. The binding of mAb-A to the dHSA coated plates was inhibited by 4 sera, enhanced in 1 and unchanged in 1 (FIG. 11). The enhanced binding of mAb-A in one experiment might seem unexpected, but can be explained by the presence of multivalent antigens to the mAb-A in cancer patient sera, which will result in formation of antigen-antibody complexes. The size of such complexes depends on the antigen/antibody ratio, thus large complexes can be formed, which still can bind to the solid phase dHSA. This will result in the binding of more mAb-A per binding site on the dHSA. In this experiment the binding of mAb-B was not reduced by incubation with cancer patient sera, probably due a high background in the experiments investigating mAb-B binding.

Taken together, these results demonstrate the presence of factors in human cancer patient sera that are bound by at least one of the antibodies, mAb-A, which is directed to dHSA and that these factors have the capacity to interfere with β2-integrin binding.

EXAMPLE 8

Demonstration of Serum Factors in Cancer Patient Sera Interfering with the Binding of Monoclonal-Antibodies Directed Against/32-Integrins—an Immunocytochemical Analysis The presence of β2-integrins on PBMCs is easily demonstrated by immunocytochemical staining. The occurrence of factors interfering with the binding of monoclonal antibodies directed against β2-integrins in cancer patient sera was analysed by staining of β2-integrins on PBMCs from healthy control persons. The presence of β2-integrin binding factors will then be demonstrated as a reduced stainability of these cells after incubation with cancer patient sera.

Figure 12:
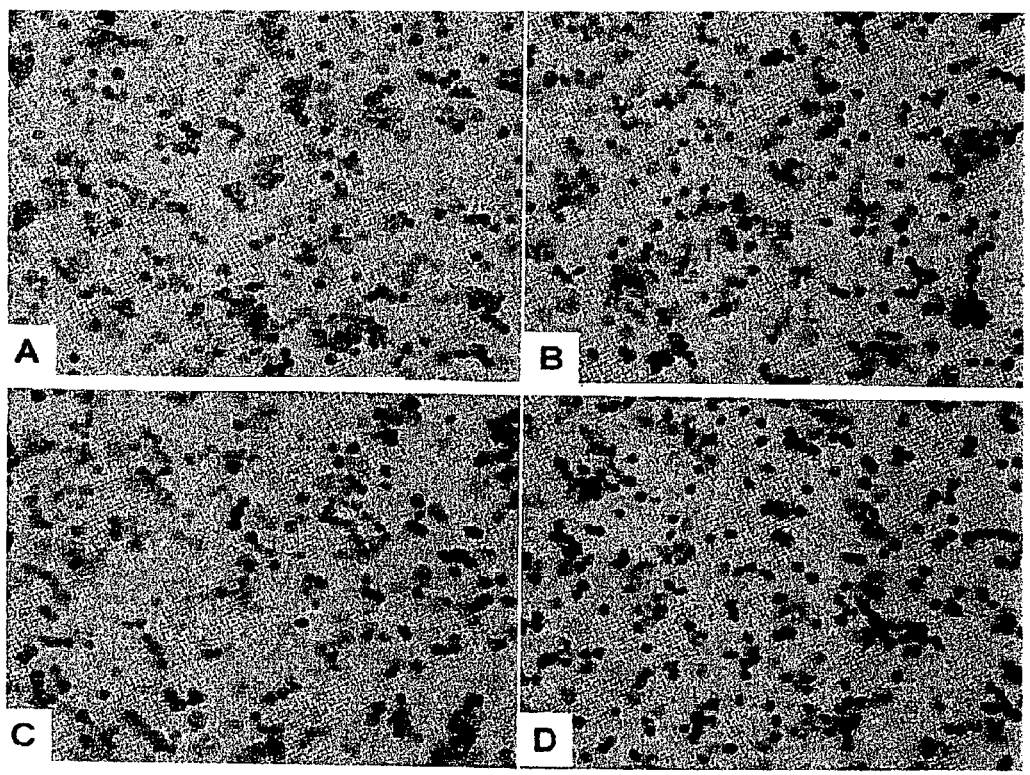
FIG. 12. Inhibition of the binding of anti-β2-integrin antibodies directed to CD18 and CD11a by incubation of normal PBMCs with patient sera. A: Control, binding of anti-CD18 after incubation with pooled human AB-serum, B: Inhibition of anti-CD18 binding after incubation with patient serum; C: Control, binding of anti-CD11 after incubation with pooled human AB-serum, D: Inhibition of anti-CD11a binding after incubation with patient serum.

Purified PBMCs, from healthy control persons, were isolated using dextran separation and density gradient centrifugation. Cytospins were then made and the cells were stained for β2-integrins, using anti-CD18 and anti-CD11a monoclonal antibodies. Pre-incubation of the cells with cancer patient sera significantly reduced the staining intensity as compared to pre-incubation with pooled sera from normal healthy blood donors. PBMCs from two different control persons were exposed to 2 and 5 patient sera respectively. Cancer patient sera reduced the staining for CD18 in 6 cases and for CD11a in 4 cases. There was also a difference in the blocking activity of the same serum for binding to different β2-integrins, that is one serum could significantly reduce the staining of CD18 without influencing the staining of CD11a and vice versa, indicating the presence of blocking factors with different specificity. All comparisons were done using the same cell preparation (FIG. 12).

EXAMPLE 9

Endogenous Antibodies Directed to dHSA

Figure 13:
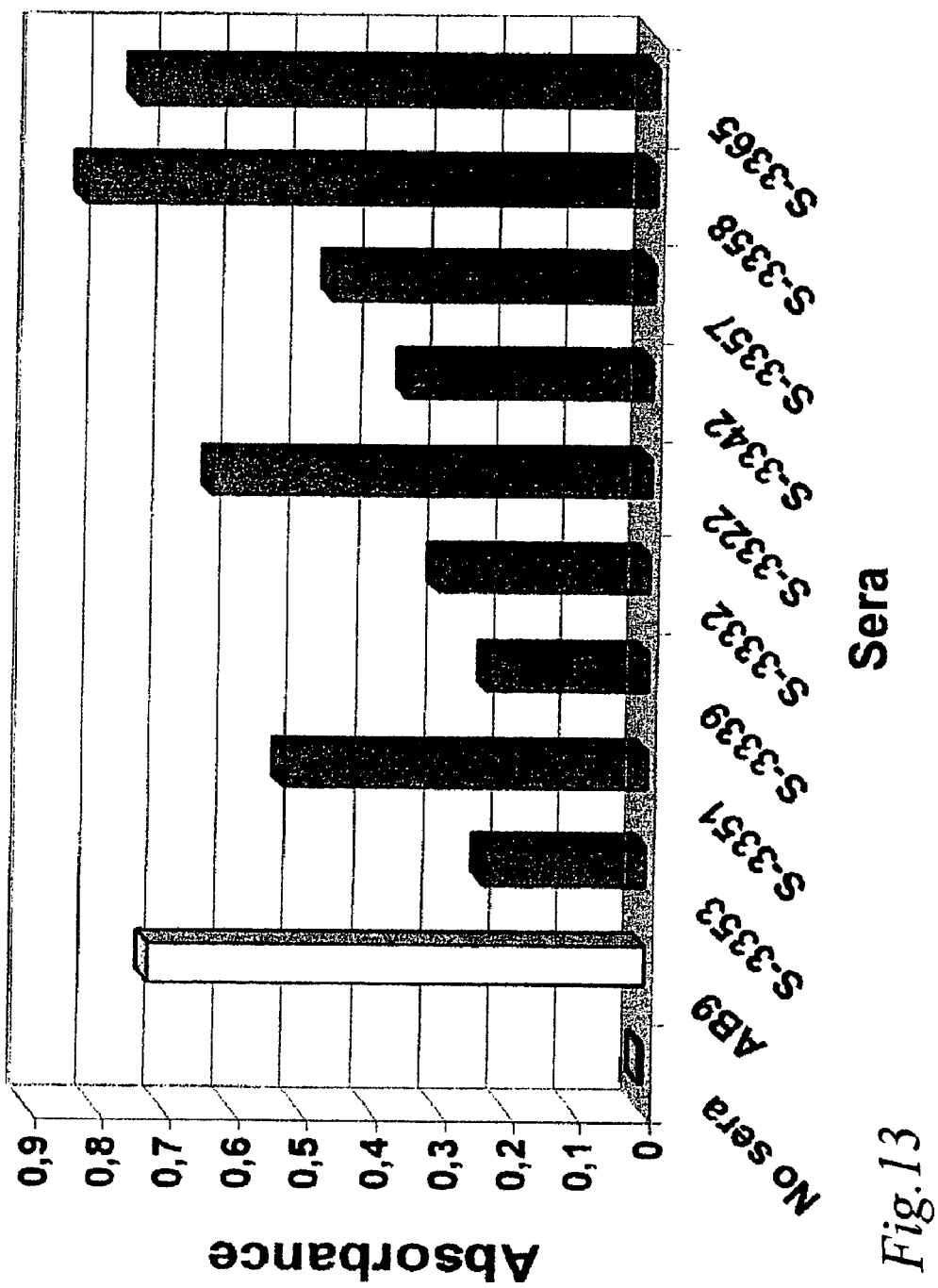
FIG. 13. The occurrence of endogenous antibodies directed against dHSA in human sera was analysed using an ELISA with plates coated with dHSA. All tested sera including the pooled control AB serum contained such antibodies with a considerable variation in concentration between different patient's sera.

The structures, which appear in HSA and other proteins upon denaturation or proteolytic fragmentation, might be antigenic neo-epitopes eliciting an immune response. Therefore, 9 cancer patient sera and a pool of 6 sera from healthy controls (AB9) were analysed for the presence of endogenous serum antibodies directed against dHSA using an ELISA technique, using plates coated with dHSA. Amazingly, all sera, including the normal pool was found to contain endogenous antibodies with reactivity to dHSA (FIG. 13). However, the binding of endogenous antibodies to the plates varied by almost a factor 4 between sera from different patients. One explanation to these results could be that HSA upon denaturation exposes structures, which via Fc-interaction or in an unspecific way binds IgG. This possibility was tested by adsorbing purified human IgG, intended for intravenous administration, on a column of dHSA bound to sepharose. In order to saturate the binding capacity of the column, which contained 10 mg dHSA, 30 mg of purified, human IgG was exposed to the dHSA at a concentration of 10 mg/ml. The column was then thoroughly washed with PBS and bound proteins were eluted with 0.1M glycine, pH 3.1. Only 13 µg protein was recovered, showing that unspecific binding of endogenous serum IgG to dHSA does not occur.

Figure 14:
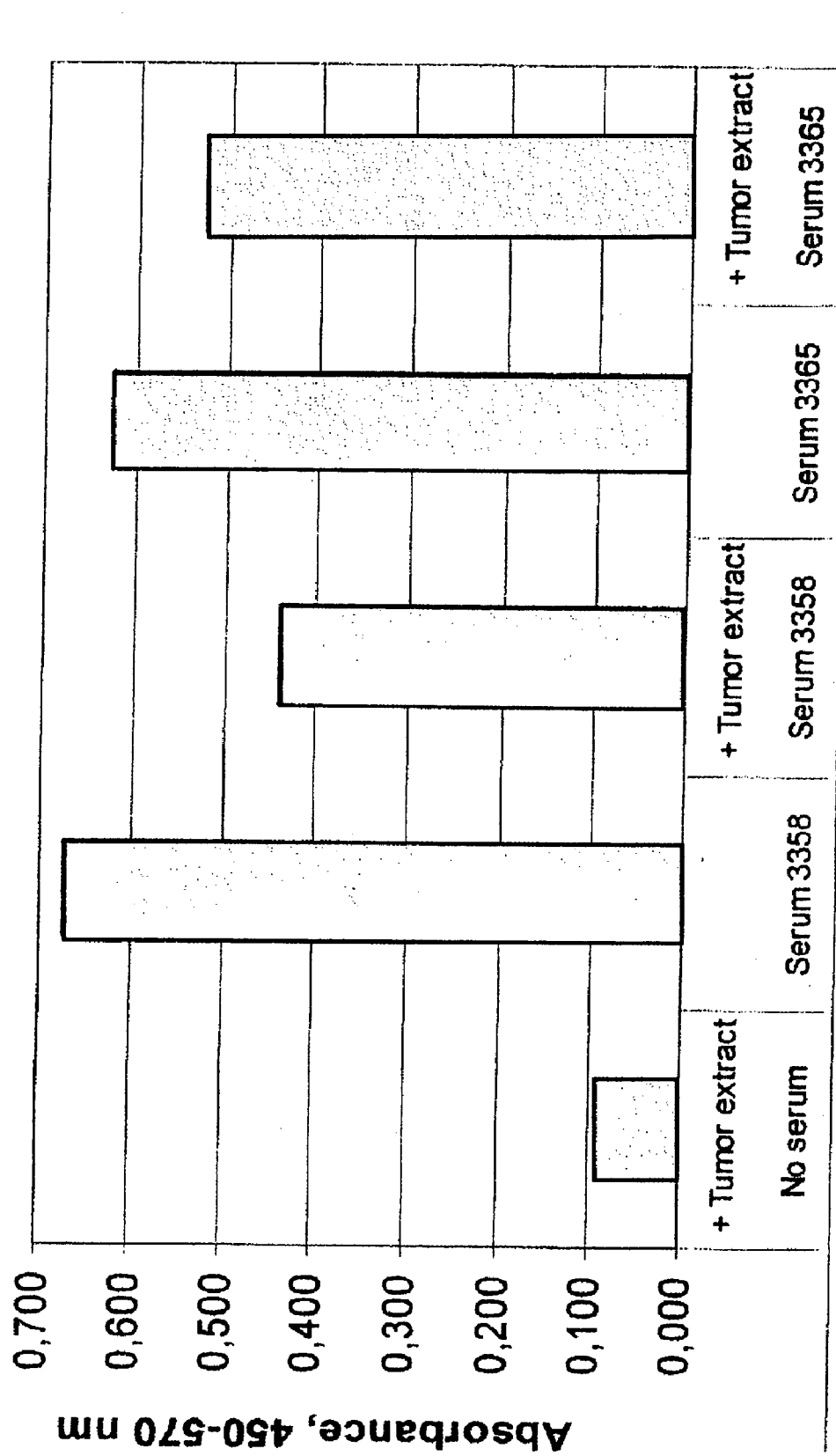
FIG. 14. ELISA for human Ig binding to polystyrene plates coated with dHSA. Sera from cancer patients (3358 and 3365) were tested alone or after pre-incubation with a tumour extract.

The relation of the endogenous antibodies to cancer was examined by preincubating sera from cancer patients with a tumour extract. As shown in FIG. 14, subsequent exposure of the incubated sera and tumour extract mixtures to dHSA coated ELISA plates indicate that there are substances present in this tumour extract which reduce the binding of endogenous serum antibodies directed against dHSA.

Competition for the same epitope on dHSA between the monoclonal antibodies mAb-A or mAb-B, and the endogenous antibodies was investigated by studying the competition of the binding of these antibodies to dHSA in an ELISA test (see Material and Methods). No competition could be identified. Furthermore, in a separate experiment the specificity of the endogenous antibodies was analysed according to the same principle as described in Example 6. Cancer patient serum was preincubated with anti-integrin antibodies (i.e. anti-CD18, anti-CD11a and anti-Cd11c) and an irrelevant control IgG1 antibody before addition to the dHSA coated plates. No antibody-antibody complexes were formed as the binding of endogenous antibodies from cancer sera to the dHSA coated plates was unchanged. This shows that antibodies to conformational changes resulting in antigenic structures of albumin, presumably related to degradation of this protein, are present in human sera but that these endogenous antibodies do not bind to β2-integrins.

The endogenous antibodies might, however, have immunoregulatory activity by binding to other substances of key importance for immune function as they are a part of the immune complexes found in sera from patients with rheumatoid arthritis (see example 10 below). As demonstrated above, the human endogenous antibodies obviously also bind to tumour epitopes (FIG. 14).

The occurrence of antibodies directed against immunoregulatory integrin binding factors will play an important role in the regulation of the immune system. β2-integrin binding factors will normally down-regulate inflammatory reactivity when an adequate concentration of these factors is reached locally. In order to avoid a systemic immunosuppression these factors can be neutralised by serum antibodies. It is thus the balance between the blocking factors and the antibodies against these factors, which determines the level of the immune/inflammatory reactivity. If the concentration of these antibodies is too high, no down-regulation of the inflammatory reactivity will take place, as can be the case in chronic inflammatory or autoimmune diseases. If on the other hand the balance is towards a predominance of blocking factors, the reactivity will be suppressed as in cancer patients.

EXAMPLE 10

Figure 15:
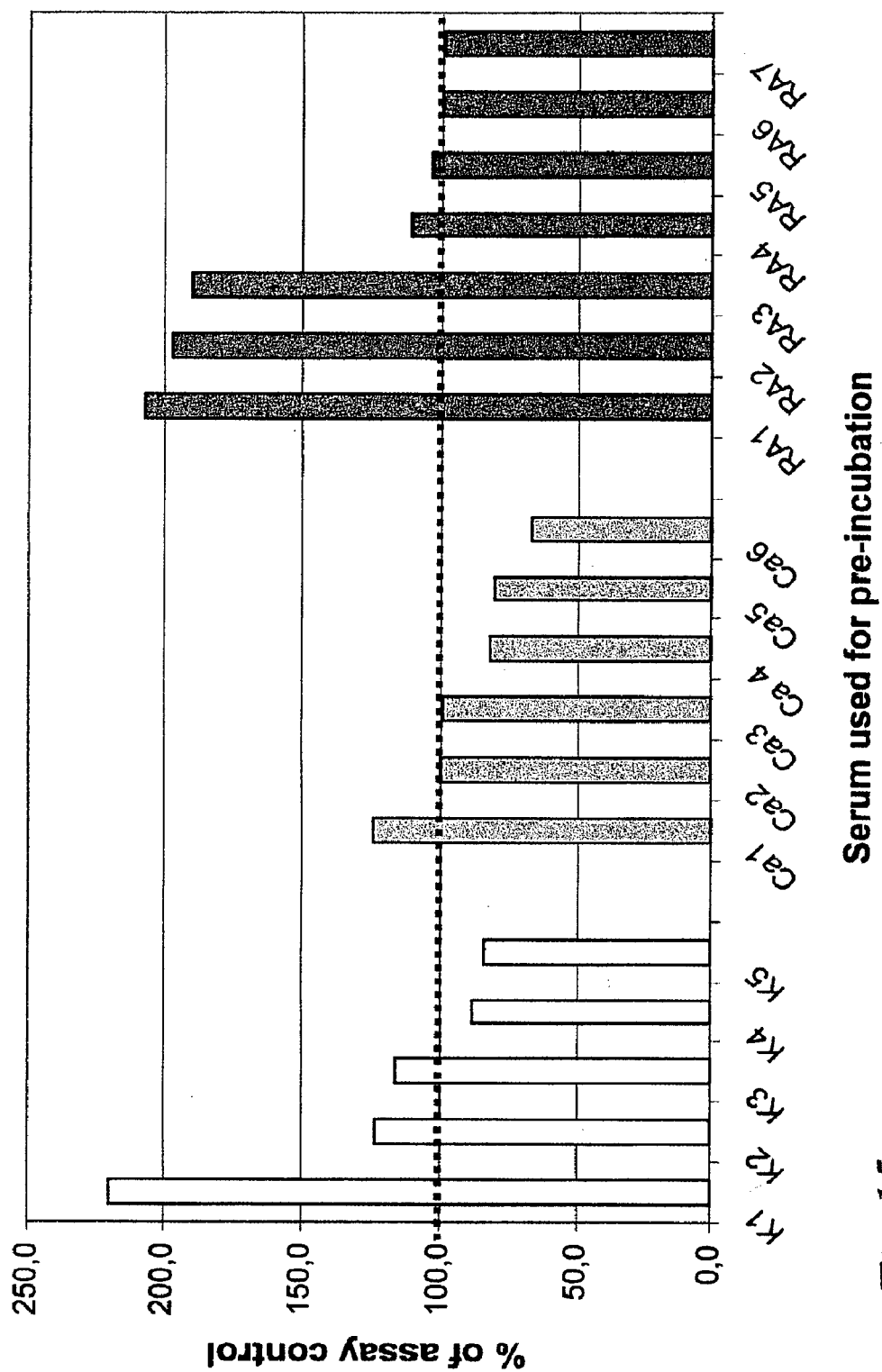
FIG. 15. Enhancement of the binding of mAb-A to dHSA after exposure of dHSA coated plated to sera from healthy controls (K), cancer patients (Ca) or patients with rheumatoid arthritis (RA) tested in an ELISA. Values are expressed as percent of control values obtained in the absence of serum.

Occurrence of B2-Integrin Binding Factors in Sera from Patients with Rheumatoid Arthritis Based on the observation that endogenous antibodies directed against neo-epitopes on dHSA are frequently present in control as well as cancer patient sera, the possible occurrence of antigen-antibody complexes including such endogenous antibodies and albumin fragments was investigated. ELISA plates coated with dHSA were incubated with sera from healthy controls, cancer patients and patients with rheumatoid arthritis. The plates were thoroughly washed and then exposed to mAb-A. An enhanced binding of serum substances containing the epitopes detected by the monoclonal antibody mAb-A was demonstrated. As shown in FIG. 15, immune complexes containing endogenous human antibodies and fragments containing the epitope identified by mAb-A were found in sera from 1/5 controls, 0/5 cancer patients and 3/7 patients with rheumatoid arthritis. The mechanism by which mAb-A binding epitopes are bound to dHSA coated ELISA plates was further analysed by pre-adsorption of sera (e.g. 2/3 of the RA sera in this experiment) by either dHSA-sepharose or protein-G-sepharose. Both adsorption procedures completely removed the immune complexes from sera, which confirms the mechanism that endogenous antibodies bind to solid phase dHSA and that these antibodies then also bind the fragment which in turn also binds the mAb-A antibody.

These results thus clearly demonstrate that immunoregulatory, β2-integrin binding epitopes present on dHSA also are present in the sera from patients with rheumatoid arthritis. As demonstrated in this invention such structures are also present in various types of human cancers (demonstrated by immunohistochemistry in Example 4), in tumour extracts (demonstrated using the SELDI technique in Example 4) and in sera from cancer patients (Examples 7 and 8). Taken together these results confirm the immunoregulatory mechanism described in this invention: that substances which downregulate and/or inhibit immune reactivity are produced in inflammation and cancer, that these substances are physiological down-regulators of an immune response, that they are produced in too small amounts or are blocked (bound in immune complexes) in patients with chronic inflammatory/auto-immune diseases and that they are produced in an excess in malignant tumours, which results in cancer related immunosuppression.

EXAMPLE 11

Effect of Neo-Structures of dHSA on Lymphocyte Proliferation

Figure 16:
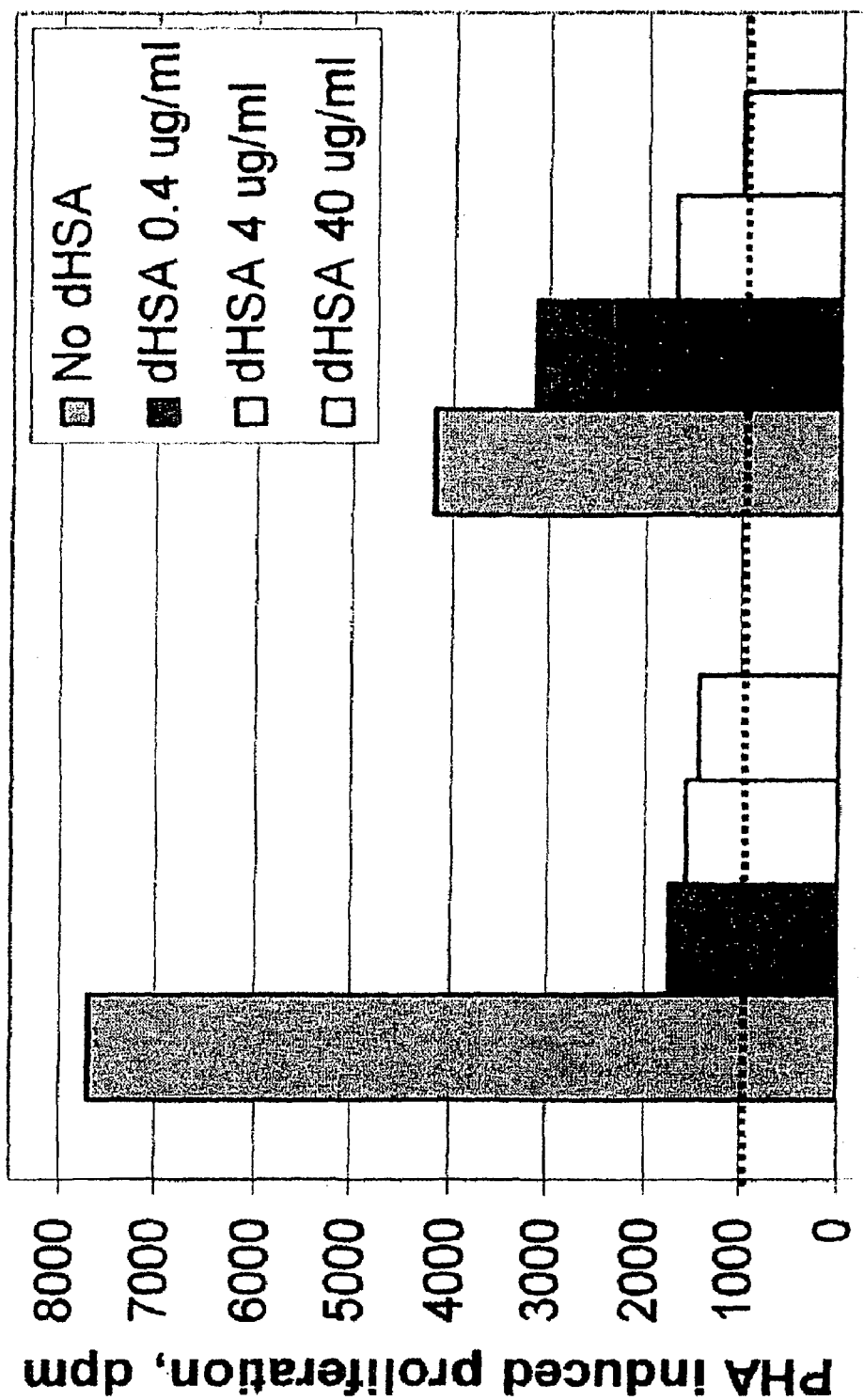
FIG. 16. Inhibitory effect of dHSA on PHA-induced proliferation of PBMCs. PBMC from two healthy controls (K113 and K114) were tested. The dotted line represents the mean proliferation of PBMC in the absence of added PHA.

Besides the pivotal role of β2-integrins in 1) the initiation of an immune response, 2) tissue recruitment and migration of inflammatory cells, 3) the cytotoxic activity of such cells, also the regulation of lymphocyte proliferation are influenced by β2-integrins. Therefore, dHSA at various concentrations was added to mitogen stimulated PBMC cultures and the effect on lymphocyte proliferation was determined as incorporation of $^3$H-thymidine. As shown in FIG. 16, dHSA markedly inhibited proliferation already at a concentration of 400 ng/ml and at 4 μg/ml it was almost completely abolished.

Figure 17:
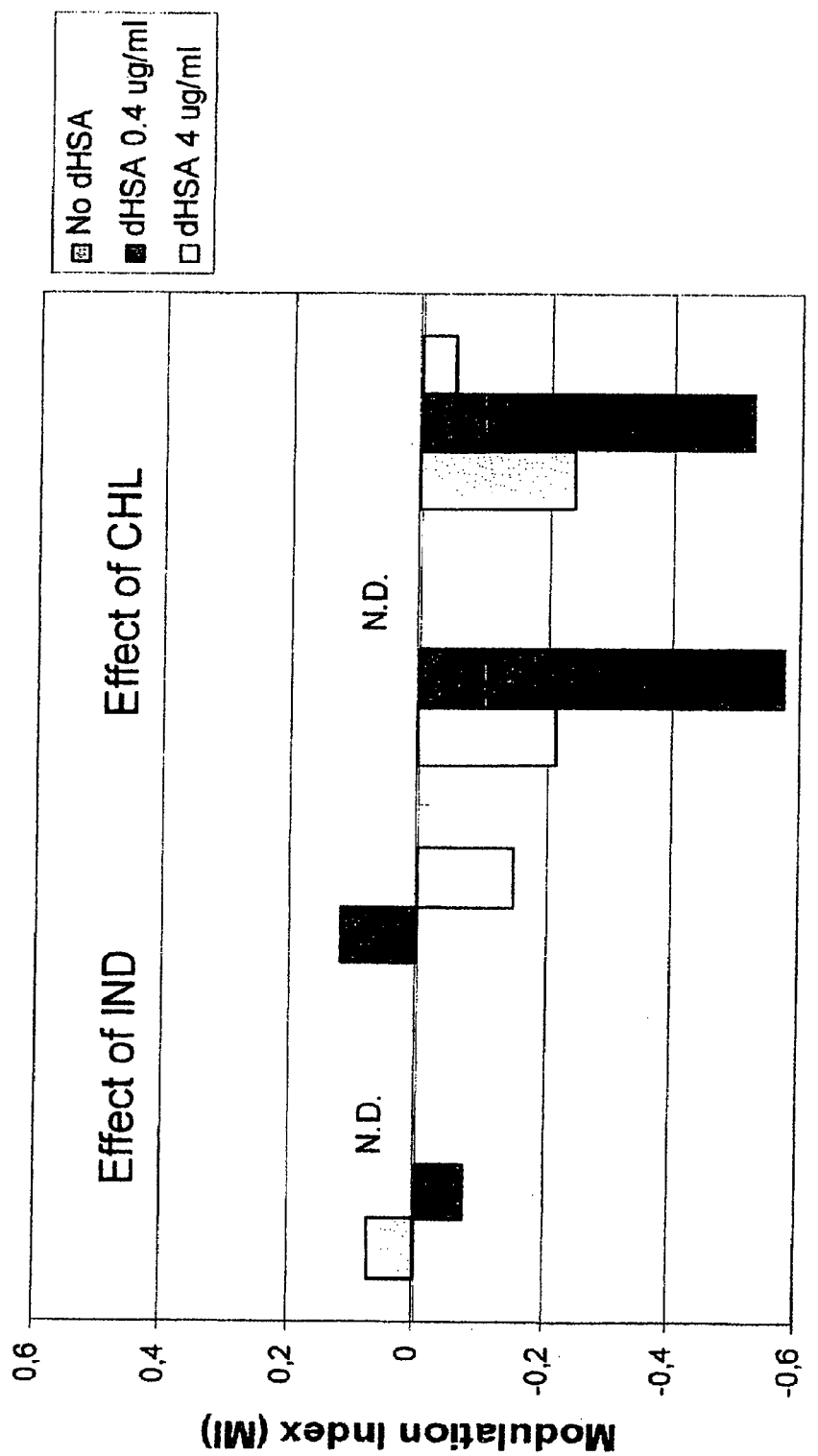
FIG. 17. Effect of dHSA (dHSA) on the ability of Indomethacin (IND) or chlorambucil (CHL) to modulate the PHA-induced proliferation of PBMCs.•PBMC from two healthy controls (K113 and K114) were tested. Modulation Index, MI=log(proliferation with PHA+drug/proliferation with PHA alone).

We have previously shown that the effect of immunomodulatory drugs on lymphocyte proliferation in mitogen stimulated PBMC cultures from cancer patients predicts response to immunotherapy. An inhibitory effect of chlorambucil identifies renal cell carcinoma patients responding to interleukin-2 and a stimulatory effect of cimetidine identifies responders to interferon-alpha (European patent no.: 0824695 (U.S. Pat. No. 6,242,202 B1) to Haakansson et al.). Based on this knowledge, the effect of dHSA on the modulatory effect of indomethacin and chlorambucil was tested in the present experiments. Only minor effects of dHSA on the modulatory effect of indomethacin were found, whereas the effect of chlorambucil was markedly influenced by addition of dHSA to the cultures (FIG. 17). Thus, dHSA neo-structures seem to be involved in the effect of immunomodulatory drugs in these predictive tests.

EXAMPLE 12

Figure 18:
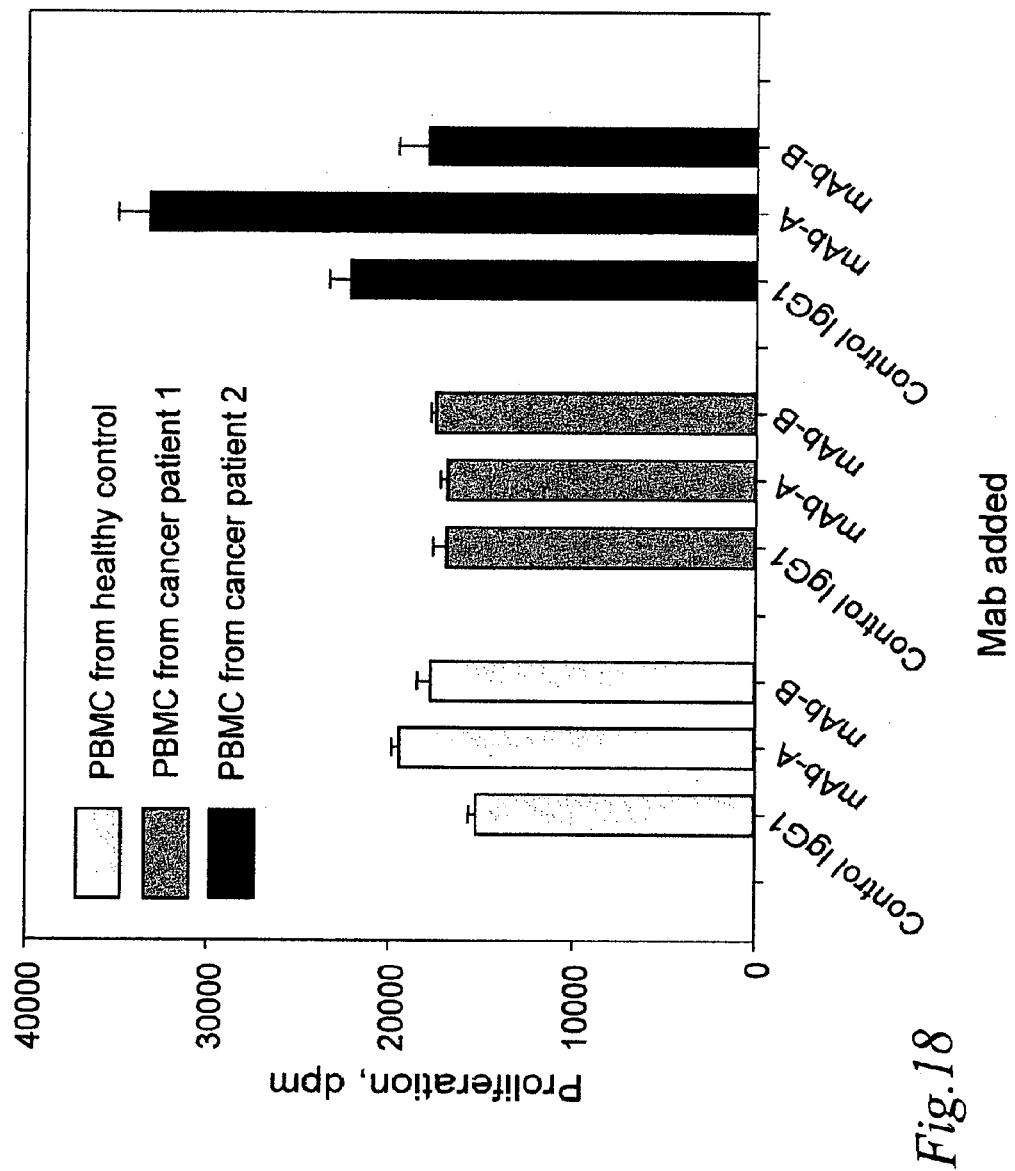
FIG. 18. Effect of mAb-A, mAb-B or an irrelevant control IgG1 antibody on the PHA-induced proliferation of PBMC from a healthy control or two different cancer patients.

Effect of Monoclonal Antibodies mAb-A and mAb-B on Mitogen Stimulated Proliferation of PBMCs from Cancer Patients As structures on dHSA inhibit mitogen-stimulated proliferation of PBL and such structures are present in sera from cancer patients, the effect of mAb-A and mAb-B on mitogen stimulated proliferation was studied. PBMCs from controls and cancer patients were cultured for 3 days using PHA as a mitogen. mAb-A and mAb-B and a control mAb (an irrelevant antibody of the same subclass) were added at the start of the cultures. The proliferative rate was determined as incorporation of 3H-TdR during the final 18 hours. mAb-A or mAb-B enhanced the proliferative rate of PBMCs from several cancer patients, a representative example is shown in FIG. 18. This experiment demonstrates that the immunosuppressive activity of epitopes present in cancer sera is inhibited when they bind to mAb-A and mAb-B as the growth rate for the PBMCs is enhanced. Similar results were obtained even when all IgG was removed from the culture medium using adsorption with surplus protein-G-sepharose beads, which shows that the stimulatory effect of adding mAb-A and mAb-B was not due to immune complexes.

The monoclonal antibodies mAb-A and mAb-B, thus have the capacity to bind and block the immunosuppressive activity of HSA related structures in cancer patients and patients with chronic inflammatory and auto-immune diseases. They are therefore of great diagnostic value for determination and monitoring of immunosuppressor activity in cancer patients and patients with chronic inflammatory and auto-immune diseases. Furthermore, these antibodies have the therapeutic capacity to abolish immunosuppression in cancer patients and thereby improve the performance status and the treatability of these patients.

Diagnostic Methods

Based on the results described above, diagnostic tests have been developed.

EXAMPLE 13

Figure 19:
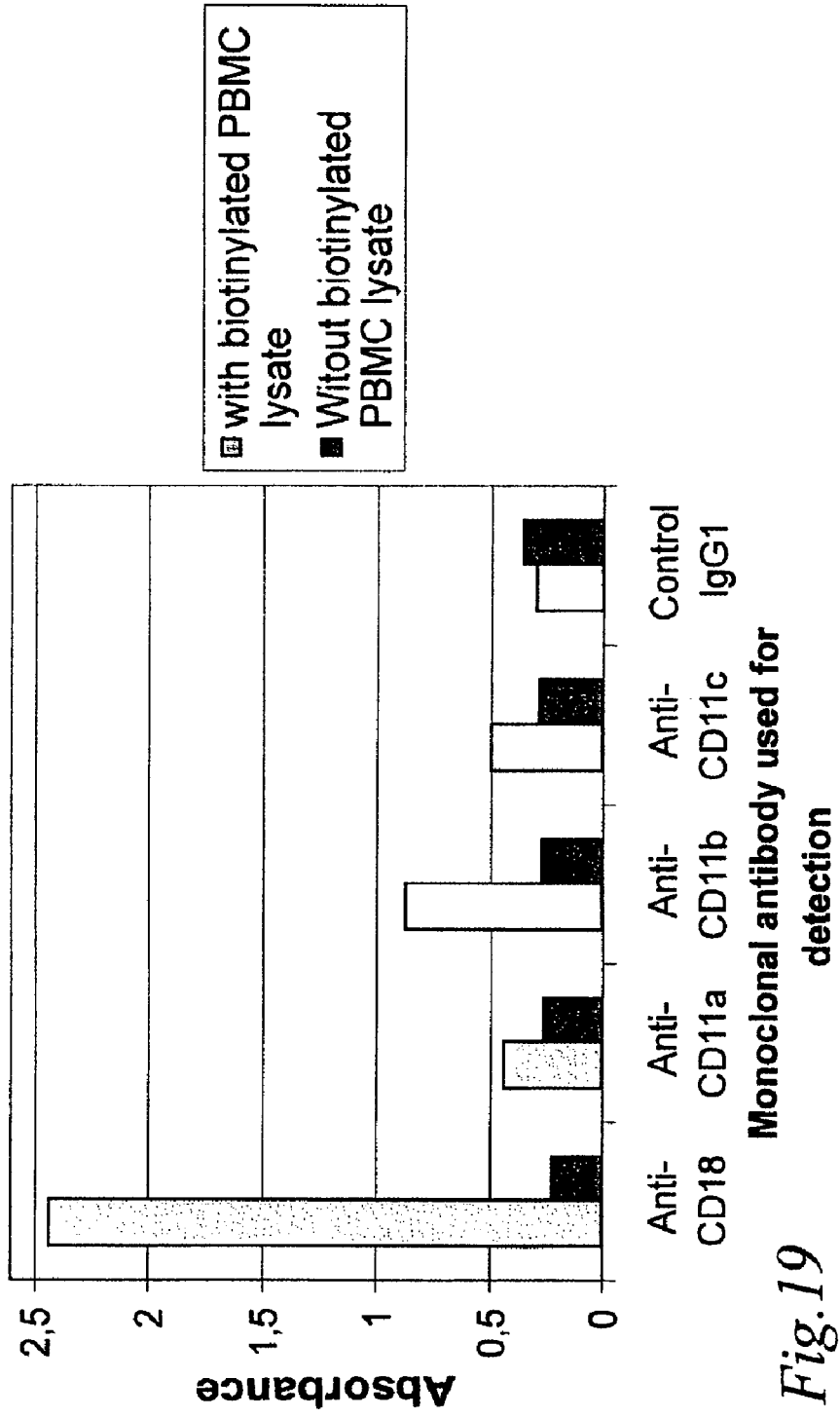
FIG. 19. Demonstration of β2 integrins in lysate from cellsurface biotinylated normal PBMCs. The lysate was incubated on strepavidin-coated plastic polystyrene plates and the binding of antibodies to CD18, CD11a, CD11b, CD11c to the lysate was tested in an ELISA.

Demonstration of 2-Integrin Binding/Blocking Factors—ELISA-Technique Using Integrin Coated Micro Titer Plates The occurrence of β2-integrin blocking factors can be demonstrated as inhibition of the binding of the specific anti-integrin monoclonal antibodies to PBMC in cytospin preparations (Example 8) or by using an. ELISA-test, wherein microtiter plates are coated with integrins The possibility to determine cell surface receptor binding/blocking factors has been further developed. In principal, the cell surface of any cell population can be made available for analysis of a large number of factors binding to a large number of cell surface receptors using the following technique: The cell surface substances of living cells are biotinylated. The cells are then dissolved in the presence of protease inhibitor and this lysate is transferred to streptavidin coated microtiter plates, which, after the binding of the biotinylated cell surface substances, are thoroughly washed. The feasibility of this technique is demonstrated in FIG. 19 where the presence of β2 integrins on microtitre plates prepared in this way were detected. Inhibition of binding to a certain receptor can then be determined as a reduced binding of the specific monoclonal antibody in the presence of a specific blocking factor. This technique can also be used to analyse the occurrence of cell surface binding substances in various body fluids such as blood, serum, plasma, urine and tissue extracts, e.g. tumour extracts, or from patients with any other type of disease. In this situation the biotinylated lysate is instead bound to streptavidin coated chromatographic gel. The solution under investigation is then absorbed by this gel, which is thoroughly washed, and the flow through solution and eluted bound substances can then be further analysed using 2D-gel electrophoresis, biological assays, or microarrays. In contrast, to using whole cells for this type of investigation, there is no risk of contamination by a large number of intra-cellular substances.

Alternatively, purified or recombinant immunoregulatory cell surface receptors can be used and antibodies directed to the functional site of these molecules will be selected for an inhibition test where the presence of a blocking factor in the test solution will inhibit/reduce the binding of the specific antibody.

The possibility to investigate cancer patients for the presence of β2-integrin receptor binding/blocking factors will give important information on the capacity of cancer patients to mount an immune response, the possibility to achieve immune mediated tumour control and respond to immunostimulatory treatment strategies. Determination of these factors will also be of great value in monitoring chronic inflammatory and autoimmune diseases.

EXAMPLE 14

Determination of Antibodies Directed Against 2-Integrin Binding/Blocking Factors The immunoregulatory integrin binding factors described in the present invention expose neo-epitopes/antigens, which can elicit an immune response including antibodies directed to these new structures. The immune status of patients can thus be modulated by development of such endogenous antibodies as they might have the capacity to neutralize the blocking factors whereby down-regulation of an immune response is counteracted. Thus, the balance between blocking factors and neutralizing antibodies determines the degree of immune reactivity. Determination of such antibodies can thus provide important prognostic information for cancer patients and patients with chronic inflammatory or autoimmune diseases.

An ELISA test for the determination of such antibodies has been developed: Microtiter plates are coated with the blocking factor, in this case dHSA, exposing blocking factor epitopes, after incubation with the antibody containing solutions, e.g blood serum or plasma, bound antibodies are measured using standard ELISA-technique. In the present investigation a frequent occurrence of endogenous human serum antibodies directed to dHSA was demonstrated (Example 9).

EXAMPLE 15

Determination of Factors Interfering with Binding of Monoclonal Antibodies Directed Against their Specific Antigens The presence of interfering factors can be determined by binding the specific antigen (dHSA) to microtiter plates. The monoclonal antibody is then incubated with the solution containing the interfering factor and the binding of the antibody to the solid phase antigen is quantified. In the present investigation, this method is used to determine the occurrence of factors interfering with the binding of anti-dHSA antibodies directed against dHSA in cancer patient sera (Example 7).

Therapeutic Possibilities/Strategies

Figure 20:
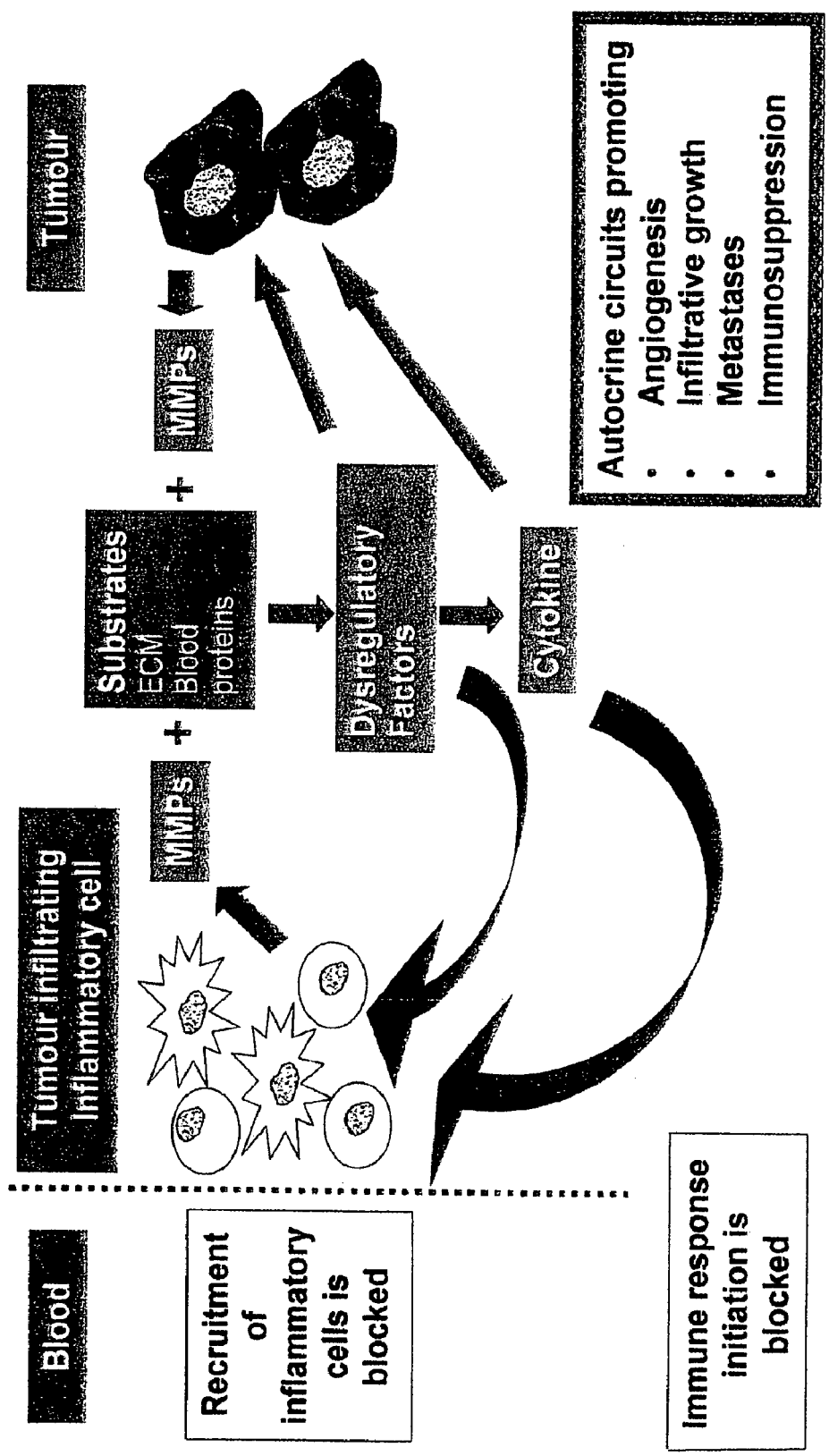
FIG. 20. Recruitment of inflammatory cells to the tumour results in autocrine circuits generating more MMPs and dysregulatory factors/cytokines, which will initiate generation of dysregulatory factors/cytokines and MMPs by tumour cells whereby autocrine circuits with tumour cells, not dependent on the presence of inflammatory cells, are established.

Removal or inhibition of immunoregulatory integrin binding factors will thus restitute the function of the immune system in cancer patients and in the case the autocrine circuits generating proteolytic enzymes (FIG. 20) also are inhibited, angiogenesis and metastatic potential will be blocked.

The neo-structures appearing in normally occurring substances after proteolytic fragmentation are highly immunosuppressive by blocking β2-integrins. They can therefore be used to efficiently inhibit the inflammatory activity in chronic inflammatory and autoimmune diseases.

Material and Methods

Reagents

Human serum albumin (HSA) infusion solution, 200 mg/ml, was purchased from Pharmacia (Uppsala, Sweden). Recombinant human albumin was from Vitrolife AB, Goteborg, Sweden. Purified human immunoglobulin for intravenous injection, GammaGard (human IgG) was purchased from Baxter AS (Allerod, Denmark).

Preparation of Peripheral Blood Mononuclear Cells (PBMC) (Examples 1, 5, 8, 11, 12, 13)

Venous blood was drawn from healthy volunteers or from cancer patients in glass vacuum tubes with acid dextrose citrate solution A as an anti-coagulant (Vacutainer, Becton & Dickinson, NJ). Erythrocytes were removed by sedimentation on 2% dextran T500 solution (Amersham Pharmacia Biotech AB, SE) in 0.9% NaCl. Mononuclear cells were then isolated by Ficoll-paque Plus (Pharmacia AB, SE) density gradient centrifugation after which the cells were washed twice in RPMI1640 Dutch's modification (RPMI) (Gibco BRL, Scotland). Cell viability was assessed by exclusion of 0.05% Trypan Blue and was always above 95%. The cell suspension was stained with Turk's solution and the number of lymphocytes and monocytes in the PBMC preparation were counted in a hemocytometer. PBMCs were suspended in RPMI and the cell concentration was adjusted to $5\times10^5$ lymphocytes/ml.

Binding of PBMC to Albumin Coupled Sepharose (Example 1)

HSA was coupled to Cyanogen bromide-activated Sepharose 4B (Amersham Biosciences, Uppsala, Sweden) following the instructions from the manufacturer. Fifty mg HSA, at a concentration of 10 mg/ml, was used per g of Sepharose. The remaining free sites were blocked according to the manufacturer's instructions. A portion of the HSA coupled Sepharose spheres was then denatured, reduced and alkylated by the addition of 8 M Urea and 10 mM dithiothretiol in 50 mM Tris-HCl (pH 8.0). The separose spheres were incubated with gentle mixing for 2 h at room temperature followed by the addition of 60 mM iodoacetamide and an additional 2 h of incubation at room temperature. They were then washed extensively in RPMI1640. The remaining portion of the HSA-coupled sepharose spheres was not denatured but resuspended in RPMI1640 directly and used as a control (native HSA-sepharose). PBMCs ($5\times10^5$) from healthy blood donors were stimulated by phorbol 12-myristate 13-acatate (PMA, Sigma Chemical CO, St. Louis, Mo.) at 50 ng/ml and mixed with 100 µl of packed sepharose gel coupled with either denatured HSA or native HSA in a total volume of 200 µl RPMI1640. The mixtures were allowed to incubate for 30° min at 37° C. with gentle agitation. A sample was removed immediately and photographs taken with an Olympus DP10 digital camera system mounted to an Olympus BX40 microscope.

Preparation of Soluble Denatured Human Albumin dHSA (Examples 2, 3, 4, 6, 7, 10 and 11)

HSA or recombinant human albumin was denatured and reduced by resuspending it at a final concentration of 10 mg/ml in 8 M urea and 10 mM dithiothretiol (both from Sigma) in 50 mM Tris-HCl (pH 7.9) for 2 h at 25° C. The HSA was then alkylated by the addition of 60 mM iodoacetamide (Sigma) and further incubated for 2 h at 25° C. in the dark. The HSA solution was diluted to a concentration of 100 µg/ml with phosphate buffered saline (PBS, Gibco BRL) and dialysedextensively against PBS using Spectra pore 4 dialysis tubing (Spectrum Europe, Breda, The Netherlands). Control HSA was prepared in parallel by incubating HSA at 10 mg/m in Tris-HCl (pH 7.9) without urea or dithiothretiol followed by dialysis. The protein concentration was determined using the Bio Rad Bradford protein assay kit following the manufacturers recommended protocol.

ELISA for the Detection of Murine Antibodies Binding to Human Albumin Coated on microtitre Plates (Examples 2, 3, 4, 6 and 7)

Duplicate wells in Hibinding microtitre plates (Costar 2592, Corning Inc, NY, USA) were coated with 100 µl of denatured HSA or recombinant human albumin diluted in PBS at the indicated concentrations or, alternatively, control HSA at the same concentration. The plates were incubated at room temperature overnight. The wells where then washed with wash buffer consisting of 0.05% Tween-20 in PBS (Sigma) followed by blocking for 1 h at 25° C. with 200 µl 0.5% gelatin prepared from bovine skin (Sigma) in PBS followed by washing in wash buffer. Either of two murine monoclonal antibodies (IgG1) with specificity for denatured, human albumin (mAb-A or mAb-B) was added at 1 or 0.5 µg/ml, respectively, in ELISA reagent diluent (0.01% gelatin (Sigma) and 0.05% Tween-20 (Sigma) in 20 mM Tris-buffered saline (TBS, SIGMA)). The antibodies were incubated for 1.5 h at 25° C. followed by washing. Envision-HRP (DakoCytomation Norden A/S, Glostrup, Denmark) was added diluted 1/10 in ELISA reagent diluent and incubated for 30 min at 25° C. followed by washing. Finally, a substrate solution consisting of $H_2O_2$ and tetramethylbenzidine (R&D Systems Europe, Ltd, Abingdon, UK) was added. The reaction was stopped with 1M $H_2SO_4$ and the optical density measured as absorbance (Abs) at dual wavelengths, 450 nm and 570 nm, with a Multiscan EX microplate reader (Labsystems).

Preparation of Cytospin with PBMC (Example 2, 5, and 8)

PBMC were separated as described and immediately spun down on pre-cleaned microscope slides in a Shandon Cytospin (Shandon Scientific Ltd, UK) at 1000 RPM for 7 min using 100 µl of the PBMC suspension at $5 \times 10^5$/ml. The slides were left to dry at room temperature over night, after which they were wrapped in parafilm and stored at −70° C. until further processed.

Detection of the Binding of Denatured Human Albumin to PMA-Stimulated PBMC by immunocytochemistry (Example 2)

PBMCs ($12 \times 10^6$/ml) from healthy controls were pre-incubated with denatured HSA at a final concentration of 100 µg/ml in PBS supplemented with 5 mM $MgCl_2$ in the presence of 50 ng/ml phorbol 12-myristate 13-acetate (PMA, Sigma) for 30 min at 37° C. The PBMCs were then washed extensively in PBS and the cell population recounted in a hemocytometer and the cell concentration adjusted to $5 \times 10^5$ lymphocytes/ml. Cytospins were prepared immediately as described above and frozen. Immunocytological detection of epitopes for denatured human albumin and the $\beta_2$-integrin CD18 are described below.

The Detection of Epitopes of Denatured Human Albumin or Human Integrins by immunocytology and Immunohistochemistry (Example 2, 4, 5 and 8)

Cytospins, from PMA-stimulated PBMC preincubated with denatured HSA (described above) or, alternatively, unstimulated PBMC from healthy controls or patients with cancer, were prepared and frozen at −70° C. Biopsies from the resected tumours were immediately snap frozen and stored at −70° C. until further processed. Cytospins or frozen tissue sections, 6-7 µm thick, were thawed and fixed with aceton for 5 min at room temperature. The cytospins and sections were first blocked with 10% normal human AB-serum for 1 h before staining. In some experiments, PBMC cytospins were pre-incubated with 10% serum from cancer patients before addition of primary antibodies. Primary antibodies, consisting of either monoclonal mouse anti-human denatured albumin (mAb-A or mAb-B) at 10 µg/ml or mouse anti-human CD18 (clone MHM23, Dakocytomation) at 2 µg/ml or mouse anti-human CD11a (clone HI111, BD Biosciences PharMingen) at 2 µg/ml, were added. The primary antibodies were diluted in Tris buffered saline (TBS, pH 7.6). They were incubated for 30 min. The slides were washed in TBS followed by Envision-Alkaline Phosphatase (Dakocytomation) for 30 min. After additional washing in TBS, the slides were incubated in alkaline phoshatase substrate consisting of Fast Red TR salt (Sigma), naphtol AS-MX (Sigma) and 5 mM levamisol (Sigma) to block endogenous alkaline phosphatase activity, for 20 min followed by washing in TBS. They were then counterstained in Mayer's haematoxylin for 1 minute and mounted in Glycergel (Dakopatts). Monoclonal mouse IgG1 against an irrelevant antigen (*Aspergillus niger* glukosoxidase, DakoCytomation) was used as a negative control. All incubations were performed at room temperature in a moist chamber.

Proteolytic Fragmentation of HSA (Example 3)

Buffer exchange to 25 mM $NH_4HCO_3$, pH8, was performed on dHSA and control HAS using PD-10 chromatography columns (Amersham Biosciences, Sweden). 0.5 ml of dHSA or native HSA (26 µg) were then incubated at 37° C. over night with increasing concentrations (4, 2, 1, 0.1, 0.01 µg) of sequencing grade modified trypsin (Promega Corporation, WI) dissolved in 50 mM $C_2H_4O_2$. Remaining trypsin in the samples was then inactivated by passage over a column consisting of 0.4 ml trypsin inhibitor coupled to 4% agarose (Sigma Chemical Company). Control samples of dHSA or native HSA with $C_2H_4O_2$ without trypsin were processed in parallel.

Analysis of Fragmented HSA with Gel Electrophoresis (Example 3)

Trypsin treated samples were diluted 1:3 in Laemmeli sample buffer (Bio-Rad Laboratories Inc) with 20% 2-mercaptoethanol (Sigma). Samples were heated to 95° C. for 5 min and 15 µl loaded per lane of Criterion Tris-HCL 4-20% precast gels (Bio-Rad Laboratories Inc). Gels were run for 1 hr in Tris/Glycine/SDS buffer (Bio-Rad). Separated protein bands were visualized with Silverstain Kit from Bio-Rad laboratories.

Interference of Trypsin Fragmented HSA with the Binding of mAb-A to dHSA (Example 3)

The trypsin treated HSA samples at a final concentration of 45% were preincubated with 1 µg/ml of mAb-A in ELISA reagent diluent for 1 h at room temperature. The HSA-antibody mixtures (100 µl) were then added to ELISA plates, which had been pre-coated with 4.5 µg/ml dHSA in PBS and blocked with 0.5% gelatin. The ELISA to detect murine antibodies binding to human albumin was then performed as described above.

Immunohistochemical Staining for the Expression of ICAM-1 on Tissue Sections (Example 4)

Biopsies from the resected tumours were immediately snap frozen and stored at −70° C. until further processed. Frozen tissue sections, 6-7 µm thick, were fixed in phosphate-buffered 4% paraformaldehyde (PFA, Riedel-de Haen Ag, Seelze, Germany) supplemented with 5.4 g/L of glucose for 5 minutes and then washed in Hank's balanced salt solution (BSS, Gibco BRL, Paisley, UK) supplemented with 0.01 M Hepes solution. Sections were blocked with 10% normal human AB-serum before staining. They were then incubated with mouse anti-human ICAM 1 (CD54, Dakocytomation at 7.5 µg/ml for 30 min. Mouse IgG1 (Dakocytomation) was used as a negative control. The slides were washed in BSS with 0.1% saponin (BSS-saponin) followed by incubation in rabbit anti-mouse IgG (Dakocytomation) diluted 1/25 in BSS-saponin for 30 min. Slides were then washed in BSS-saponin and incubated with APAAP (Dakocytomation) diluted 1/25 in BSS-saponin for 30 min. After washing in BSS-saponin and TBS, the slides were incubated in alkaline phoshatase substrate consisting of Fast Red TR salt (Sigma), naphtol AS-MX (Sigma) and 5 mM levamisol (Sigma) to block endogenous alkaline phosphatase activity, for 20 min followed by washing in TBS. They were then counterstained in Mayer's haematoxylin for 1 minute and mounted in Glycergel (Dakopatts). All antibody solutions also contained 2% normal human AB serum.

Preparation of Tumour Extracts (Example 4)

Biopsies of 0.5-1 cm in diameter from 6 patients diagnosed with renal cell carcinoma and one patient diagnosed with malignant melanoma were embedded in glycergel (Dakopatts) and immediately snap-frozen in liquid nitrogen. Frozen biopsies were kept at −70° C. until use. Each biopsy was processed individually. Five to ten tissue sections were cut (50 μm) from each biopsy and thawed on ice. The sections were then carefully rinsed with ice-cold RPMI1640 with 200 IU/ml penicillin and 200 mg/ml of streptomycin (RPMI/PEST, Gibco BRL). The sections were transferred to a solution of RPMI/PEST containing 10 mM EDTA (Sigma), 1 μM pepstatin, 100 μM leupeptin and 0.5 mM Pefablock (Roche Diagnostics Scandinavia AB) for protease inhibition and immediately homogenized in a Micro-dismembrator S (B. Braun Biotech International) at 2000 RPM for 20 sec. The homogenized tissue was then resuspended in 5-19 ml cold RPMI/PEST and centrifuged at 4500 RPM for 30 min. The supernatants were decanted and saved at −70° C.

Tumour Extracts Interfering with Binding of mAb-A to dHSA (Example 4)

Each tumor extract, at a final concentration of 45%, was mixed with μg/ml of mAb-A in ELISA reagent diluent for 1 h at room temperature. The serum-antibody mixtures (100 μl/well) were then added to ELISA plates that had been pre-coated with 4.5 μg/ml denatured HSA in PBS and blocked with gelatin. The ELISA for the detection of bound murine antibodies was then performed as described above.

Detection by Surface-Enhanced Laser Desorption/Ionization Time-of-flight Mass Spectrometry (SELDI) of Proteins in Tumour Extracts Binding to a Monoclonal Antibody Specific for denatured albumin (Example 4)

Mouse anti-denatured human albumin (mAb-A) (0.5 ng) was coupled to a PS20 chip array (Ciphergen Biosystems, Inc, Freemont Calif.), deactivated with 0.5 M ethanolamine for 30 min and washed three times with PBS+0.5% Triton X and three times with PBS. The same concentration of an irrelevant, isotype matched antibody (MOPC21, Sigma) was used as a control. Ten μl of tumor extract was added and samples were incubated over night at +4° C. with mild agitation. Unbound proteiris were removed by washing three times with PBS+0.5% Triton-X and two times with PBS, followed by 1 mM Hepes. Finally, 2×0.6 μl Matrix in 50% SPA was added and the protein profiles analysed in a ProteinChip System mass spectrometer (Ciphergen Biosystems).

Determination of Antibody Specificity; the Interaction of Anti-/$\beta_2$ Integrin Antibodies with mAb-A and mAb-8 (Example 6)

The following anti-$\beta_2$ integrin monoclonal antibodies, diluted in ELISA reagent diluent at a concentration of 1 μg/ml, were pre-incubated with either mAb-A or mAb-B (also at 1 μg/ml) for one hour at room temperature; anti-human CD18 (Dako cytomation), anti-human CD11 (BD Biosciences PharMingen), anti-human CD11 (Dako cytomation), anti-human CD11 (BD Biosciences PharMingen) or negative control IgG1 (Dako cytomation). All monoclonal antibodies were murine IgG1. All antibodies had been purified with Protein G affinity chromatography either by our laboratory (anti-CD18 and anti-CD11b) or by the manufacturer. The antibody mixtures were then added to ELISA plates (100 μl/well) that had been pre-coated with 4.5 μg/ml denatured HSA in PBS and blocked with gelatin. The ELISA to detect bound murine antibodies binding to human albumin was then performed as described above.

Collection of Sera (Example 7, 8 and 9)

Serum was collected from healthy blood donors and from patients with cancer or rheumatoid arthritis (S-20, S-42, S-58, S-65, S-3320, S-3342, S-3348, S-3357 and S-3358 were diagnosed with renal cell carcinoma. S-3322, S-3332, S-3339, S-3351, S-3353 and S-3365 were diagnosed with malignant melanoma. All sera, except those used in example 11 and 12, were heat-inactivated at 56° C. for 30 min. A pool (AB9) was prepared with sera from 5 healthy AB positive blood donors. The sera were kept frozen at −70° C. until use.

Serum Factors Interfering with the Binding of mAb-A to Denatured Albumin (Example 7)

Each serum, at a final concentration of 10%, was mixed with 1 μg/ml of monoclonal antibody mAb-A in ELISA reagent diluent for 1 h at room temperature. The serum-antibody mixtures (100 μl/well) were then added to ELISA plates that had been pre-coated with 4.5 μg/ml denatured HSA in PBS and blocked with gelatin. The ELISA for the detection of bound murine antibodies binding to human albumin was then performed as described above.

ELISA for the Detection of Endogenous Human Serum Antibodies Binding to dHSA (Example 9)

Duplicate wells in Hibinding microtitre plates (Costar 2592, Corning Inc, NY, USA) were coated with 100 μl of dHSA or control HSA diluted in PBS at 4.5 μg/ml. The plates were incubated at room temperature for 2 h. The wells where then washed with wash buffer consisting of 0.05% Tween-20 in PBS (Sigma) followed by blocking for 2 h at 25° C. with 200 μl 0.5% gelatin prepared from bovine skin (Sigma) in PBS followed by washing in wash buffer. 100 μl of a 10% serum solution in ELISA reagent diluent was added to the wells and incubated for 2 h at room temperature followed by washing in wash buffer. Biotinylated goat anti-human Ig (Sigma) diluted 1/7000 in ELISA reagent diluent was then added and allowed to incubate for 1.5 h at room temperature. The plates were again washed in wash buffer. 100 μl/well of horseradish peroxidase (HRP)-coupled avedin (R&D Systems) diluted 1/200 in ELISA reagent diluent was then added and incubated for 25 min and the plates washed. Finally, substrate solution consisting of $H_2O_2$ and tetramethylbenzidine (R&D Systems Europe, Ltd, Abingdon, UK) was added. The reaction was stopped with 1M $H_2SO_4$ and the optical density measured as absorbance (Abs) at dual wavelengths, 450 nm and 570 nm, with a Multiscan EX microplate reader (Labsystems).

Detection of Endogenous Human Antibodies Binding to Denatured Albumin after Pre-Incubation of Human Sera with Tumour Extract (Example 9).

A tumour biopsy (approximately 0.8 cm in diameter) from a patient with renal cell carcinoma was embedded in glycergel (Dakopatts AB) and frozen at −70° C. For generation of tumour extracts, the biopsy was washed extensively in cold RPM1640 with 200 IU/ml penicillin and 200 μg/ml streptomycin (RPMI/PEST) (Gibco BRL) and then homogenized in a Micro-Dismembrator S at 1500 RPM for 20 s. The homogenized sample was then washed three times in ice cold RPMI/PEST and the supernatants (approximately 16 ml) collected and filterer sterilized. They were frozen at −70° C. until further use. Serum from either of two cancer patients were mixed with the tumour extract at a final concentration of 1% and 50%, respectively, in ELISA reagent diluent. The mixture was added to ELISA poystyrene plates pre-coated with denatured albumin (4.5 μg/ml) and blocked as described. Alternatively, the sera and the tumour extract were also added alone. ELISA for detection of human endogenous antibodies was then performed as previously described.

Analysis of the Competition for Epitopes Between Monoclonal Antibodies Specific for Denatured Albumin and Endogenous Antibodies in Human Sera (Example 9).

Mouse anti-denatured human albumin (mAb-A or mAb-B) at 10 μg/ml in ELISA reagent diluent was added to ELISA poystyrene plates pre-coated with dHSA (4.5 μg/ml) and blocked as described. After incubation for 1.5 h at room temperature the wells were washed with wash buffer. Sera collected form different cancer patient were diluted to 10% in ELISA reagent diluent and 100 μl added per well. The ELISA was then performed as described above for detection of human endogenous antibodies.

Analysis of the Interaction of Monoclonal Anti-Integrin Antibodies and Endogenous Human Serum Antibodies Binding to Denatured Human Albumin (Example 9).

Mouse anti-integrin antibodies; anti-CD18 (clone MHM23, Dakocytomation), anti-human CD11a (clone HI111, BD PharMingen), anti-CD11c (clone B-ly6, BD PharMingen), or an irrelevant isotype control antibody (Daocytomation) were co-incubated at 10 μg/ml for 1 h at room temperature with different cancer sera diluted to 10% in ELISA reagent diluent. 100 μl/well of the mixture was added to ELISA poystyrene plates pre-coated with dHSA (4.5 μg/ml) and blocked as described. The ELISA was then performed as described above for detection of endogenous human antibodies.

Detection of Antigen-Antibody Complexes Recognized by a Murine Monoclonal Antibody specific for denatured human albumin in sera from patients with cancer, Rheumatoid Arthritis or Normal Controls (Example 10).

Duplicate wells in Hibinding microtitre plates (Costar 2592, Corning Inc, NY, USA) were coated with 100 μl of denatured HSA diluted in PBS at 4.5 μg/ml or, alternatively, control HSA at the same concentration. The plates were incubated at room temperature overnight. The wells where then washed with wash buffer consisting of 0.05% Tween-20 in PBS (Sigma) followed by blocking for 1 h at 25° C. with 200 μl 0.5% gelatin prepared from bovine skin (Sigma) in PBS followed by washing in wash buffer. Serum diluted to 10% in ELISA reagent diluent (0.01% gelatin (Sigma) and 0.05% Tween-20 (Sigma) in 20 mM Tris-buffered saline (TBS, SIGMA)) was added and incubated for one hour at room temperature. After extensive washing in wash buffer, 1 μg/ml of murine monoclonal antibody with specificity for dHSA (mAb-A) was added and incubated for 1.5 hours at room temperature. Again the wells were washed with wash buffer. Envision-HRP (DakoCytomation Norden A/S, Glostrup, Denmark) was added diluted 1/10 in ELISA reagent diluent and incubated for 30 min at 25° C. followed by washing. Finally, a substrate solution consisting of $H_2O_2$ and tetramethylbenzidine (R&D Systems Europe, Ltd, Abingdon, UK) was added. The reaction was stopped with 1M $H_2SO_4$ and the optical density measured as absorbance CAbs) at dual wavelengths, 450 nm and 570 nm, with a Multiscan EX microplate reader (Labsystems).

Analysis of PHA-Induced Proliferation of PBMC; Effect of Denatured Albumin (Example 11).

$5 \times 10^4$ PBMC from healthy blood donors in a final volume of 200 μl were seeded into round-bottomed microtiter plates (Corning Inc. NY, US) in culture medium consisting of RPMI 1640 supplemented with 100 IU/ml Penicillin, 100 μg/ml Streptomycin and 10% heat-inactivated, autologous fresh serum. The serum had first been adsorbed by passage over a column of dHSA-coupled sepharose spheres (prepared as described in example 1). Phytohemagglutinin (PHA, Sigma) at a final concentration of 20 μg/ml, chlorambucil (CHL, Sigma), at a final concentration of 1 μg/ml, Indomethasin (IND, Sigma) at a final concentration of 1 μg/ml and/or sterile filtered, denatured HSA, at different concentrations, were then added to indicated wells. Cells were cultured for 3 days in a humidified 5% $CO_2$ atmosphere at 37° C. Proliferation was assayed by incorporation of 1.6 μCi/well of [$^3$H]thymidine (Amersham Int, UK) during the last 18 h. Mean values of dpm (disintegrations per minute) of triplicate cultures were used for the calculations.

Analysis of PHA-Induced Proliferation of PBMC; Effect of Murine Monoclonal Antibodies Binding to Denatured HSA (Example 12).

A culture medium consisting of RPMI 1640 supplemented with 100 IU/ml Penicillin, 100 μg/ml Streptomycin and 20% fresh, heat-inactivated, autologous serum was prepared. Monoclonal antibodies (mab) specific for denatured HSA (mAb-A or mAb-B) or an isotype-matched, irrelevant control antibody (MOPC21, Sigma) were added at a final concentration of 5 μg/ml to the culture medium and incubated for 30 min at room temperature. In some experiments immunoglobulins were then adsorbed from the culture medium/mab mixture by addition of protein G coupled Sepharose™ 4 Fast Flow (Amersham Biosciences). 0.4 ml swelled sepharose gel was used per 2 ml medium/mab mixture. After incubation for 1 hour at room temperature, the sepharose was pelleted by centrifugation at 500×G and the medium/mab mixture supernatant was harvested and used as culture medium. One hundred ml of the culture medium/mab mixture was added to triplicate wells of round-bottomed microtiter plates (Corning Inc. NY, US) followed by the addition of 100 μl of PBMC ($5 \times 10^4$) resuspended in RPMI 1640. Finally, phytohemagglutinin (PHA, Sigma) was added at a final concentration of 20 μg/ml and the microtiter plates were cultured for 3 days in a humidified 5% $CO_2$ atmosphere at 37° C. Proliferation was assayed by incorporation of 1.6 μCi/well of [$^3$H]thymidine (Amersham Int, UK) during the last 18 h. Mean values of dpm (disintegrations per minute) of triplicate cultures were used for the calculations.

Demonstration of (32 Integrin Binding Factors-ELISA-Technique Using Integrincoated Microtitre Plates (Example 13)

In the first step solubilized, biotinylated cell surface proteins were prepared as follows: PBMC were prepared from buffy coats with dextran sedimentation and Ficoll density centrifugation as described above. The PBMC were then suspended in phophate buffered saline (PBS) containing Ca and Mg (GIBCO) at a concentration of $10 \times 10^6$/1 ml. Sulfo-NHS-biotin (Pierce) was added at a final concentration of 0.2 mg/ml and the mixture incubated on a shaker at room temperature for 10 min. Excess biotin was then removed by washing the PBMC in PBS. The biotinylated PBMC were then lysed by adding ice-cold lysing buffer (50 mM Tris-HCL, pH 7.5, with 0.15 M NaCl, 5 mM $MgCl_2$ containing 100 mM Octyl glucoside and 1 mM Phenylmethylsulfonyl fluoride) to pelleted cells. The cell suspension was incubated on ice for 30 min. Debris was removed by centrifugation at 5000×g at 4° C. for 10 min and the supernatants collected.

In step two biotinylated cell surface proteins from lysed PBMC were immobilized on strepavedin coated microtitre plates; One hundred μl of cell lysate (representing lysate from $4 \times 10^6$ biotinylated PBMC) was added per well to EvenCoat streptavidin microplates (R&D Systems, Inc) and incubated for 30 min at room temperature. The wells were then washed four times with wash buffer (0.05% Tween-20 in PBS). The wells were then filled with 100 μl of PBS with Ca and Mg and the microplates were covered with parafilm and saved at 4° C. over night.

In step three microplate bound integrins were detected with either of the following specific monoclonal antibodies; anti-CD18 (clone MHM23, Dakocytomation), anti-human CD11a (clone HI111, BD PharMingen), anti-CD11b (clone 2LPM19c, Dakocytomation), anti-CD11c (clone B-ly6, BD PharMingen), or an irrelevant isotype control antibody (Daocytomation) were added to the wells at concentration of 1 μg/ml. The microtitre plates were incubated for 2 hours at room temperature after which they were washed four times in ELISA wash buffer (0.05% Tween-20 in PBS). Envision-HRP (DakoCytomation Norden A/S, Glostrup, Denmark) was added diluted 1/10 in ELISA reagent diluent and incubated for 30 min at 25° C. followed by washing. Finally, a substrate solution consisting of $H_2O_2$ and tetramethylbenzidine (R&D Systems Europe, Ltd, Abingdon, UK) was added. The reaction was stopped with 1M $H_2SO_4$ and the optical density measured as absorbance (Abs) at dual wavelengths, 450 nm and 570 nm, with a Multiscan EX microplate reader (Labsystems).

REFERENCES

Anderson D C, Miller L J, Schmalstieg F C, Rothlein R, Springer T A. 1986. Contributions of the Mac-1 glycoprotein family to adherence-dependent granulocyte functions: Structure-function assessments employing subunit-specific monoclonal antibodies. J Immunol 137: 15-27.

Davis G E. 1992. The Mac-1 and p150,95 β2 integrins bind denatured proteins to mediate leukocyte cell-substrate adhesion. Exp. Cell Res. 200:242-252.

Davis G E, Scott T, Madden S. 1997. The α4β1 integrin can mediate leukocyte adhesion to casein and denatured protein substrates. J Leuk Biol 62:318-328.

Håkansson A, Gustafsson B, Krysander L, Håkansson L. 1996. Tumour-infiltrating lymphocytes in metastatic malignant melanoma and response to interferon alpha treatment. Br J. Cancer. 74:670-676.

Håkansson A, Gustafsson B, Krysander B, Hjelmqvist B, Rettrup B, Håkansson L. 2001. Biochemotherapy of metastatic malignant melanoma. Predictive value of tumour-infiltration lymphocytes. Br J Cancer 85:1871-1877.

ABBREVIATIONS

BSS; Hank's balanced salt solution
CHL; Chlorambucil.
ConA; Concanavalin A
CRP; C-reactive protein
CTL; Cytotoxic T-lymphocyte
DC; Dendritic cell
ELISA; Enzyme linked immunosorbent assay
ESR; Erythrocyte sedimentation rate
FcR; Fc receptor
HRP; Horse radish peroxidase
HSA; Human serum albumin
IHC; Immunohistochemistry
ICAM-1; Intracellular adhesion molecule-1
IL-4; Interleukin-4
IL-6; Interleukin-6
IL-10; Interleukin-10
NK-cell; Natural killer cell.
IND; Indomethasin
LAD; Leukocyte adhesion deficiency
LF A-1; Leukocyte function associated antigen-1
MHC 1; Major histocompatibility complex 1
PBMC; Peripheral blood mononuclear cell
PBS; Phosphate buffered saline
PEST; Penicillin/Streptomycin
PGE2; Prostaglandin $E_2$
PHA; Phytohemagglutinin A
PMA; Phorbol myristate acetate
TAM; Tumour infiltrating macrophage
TBS; Tris buffered saline
TCR; T cell receptor
TGF-β; Transforming growth factor beta
TIL; Tumour infiltrating lymphocyte
TIMC; Tumour infiltrating mononuclear cell
TNF-α; Tumour necrosis factor a

What is claimed is:

1. A method of indicating the presence of a factor in a biological sample of a rheumatoid arthritis patient that inhibits the binding of an antibody or fragment thereof, which is specific for denatured human serum albumin comprising:
    providing a biological sample from a patient;
    contacting said biological sample with an antibody or fragment thereof, which is specific for denatured human serum albumin;
    contacting said biological sample and said antibody or fragment thereof with denatured human serum albumin; and
    detecting the amount of binding of said antibody or fragment thereof to said denatured human serum albumin, wherein an inhibition in binding of said antibody or fragment thereof to said denatured human serum albumin indicates the presence of said factor in said biological sample.

2. The method of claim 1, wherein said biological sample comprises human serum.

3. A method of indicating the presence of a factor in a sample of human serum from a rheumatoid arthritis patient that inhibits the binding of an antibody or fragment thereof, which is specific for denatured human serum albumin comprising:
    providing a sample of human serum;
    contacting said sample with an antibody or fragment thereof, which is specific for denatured human serum albumin;
    contacting said sample and said antibody or fragment thereof with denatured human serum albumin; and
    detecting the amount of binding of said antibody or fragment thereof to said denatured human serum albumin, wherein an inhibition in binding of said antibody or fragment thereof to said denatured human serum albumin indicates the presence of said factor in said sample of human serum.

4. A method of indicating the presence of a factor in a biological sample of a rheumatoid arthritis patient that inhibits the binding of an antibody or fragment thereof, which is specific for denatured human serum albumin, comprising:
    contacting a biological sample from a patient with denatured human serum albumin and an antibody or fragment thereof, which is specific for denatured human serum albumin; and
    detecting the binding of said antibody or fragment thereof to said denatured human serum albumin, wherein an inhibition in binding of said antibody or fragment thereof to said denatured human serum albumin indicates the presence of said factor in said biological sample.

5. The method of claim 4, wherein said biological sample comprises a human serum.

6. A method of indicating the presence of a factor in a sample of human serum from a rheumatoid arthritis patient that inhibits the binding of an antibody or fragment thereof, which is specific for denatured human serum albumin comprising:
    contacting a sample of human serum with denatured human serum albumin and an antibody or fragment thereof, which is specific for denatured human serum albumin; and
    detecting the binding of said antibody or fragment thereof to said denatured human serum albumin, wherein an inhibition in binding of said antibody or fragment thereof to said denatured human serum albumin indicates the presence of said factor in said sample of human serum.

* * * * *